(12) United States Patent
Schreiber et al.

(10) Patent No.: US 9,050,458 B2
(45) Date of Patent: Jun. 9, 2015

(54) POINT OF CARE RADIOACTIVE MATERIAL STRANDING SYSTEMS

(71) Applicant: THERAGENICS CORPORATION, Buford, GA (US)

(72) Inventors: David Schreiber, Littleton, CO (US); Jack C. White, Alpharetta, GA (US); David Wesley Stephens, Cornelia, GA (US); Henry C. Goode, Atlanta, GA (US); Nathan Christopher Griffith, Lawrenceville, GA (US); Ming K. Tai, Lawrenceville, GA (US)

(73) Assignee: Theragenics Corporation, Buford, GA (US)

( * ) Notice: Subject to any disclaimer, the term of this patent is extended or adjusted under 35 U.S.C. 154(b) by 0 days.

(21) Appl. No.: 13/733,272

(22) Filed: Jan. 3, 2013

(65) Prior Publication Data
US 2013/0190549 A1  Jul. 25, 2013

Related U.S. Application Data

(62) Division of application No. 11/877,339, filed on Oct. 23, 2007, now Pat. No. 8,360,951.

(51) Int. Cl.
*A61N 5/10* (2006.01)

(52) U.S. Cl.
CPC ....... *A61N 5/1001* (2013.01); *A61N 2005/1009* (2013.01); *A61N 2005/1023* (2013.01)

(58) Field of Classification Search
CPC .............. A61N 5/1001; A61N 5/1027; A61N 2005/1001; A61N 2005/1009; A61N 2005/1023; A61N 2005/1024
USPC ......................................................... 600/1–8
See application file for complete search history.

(56) References Cited

U.S. PATENT DOCUMENTS 4,086,914 A    5/1978  Moore
4,167,179 A    9/1979  Kirsch
(Continued)

FOREIGN PATENT DOCUMENTS

WO    9722379       6/1997
WO    9722379 A2    6/1997

OTHER PUBLICATIONS

Shuying Wan, Chandra P. Joshi, Greg Carnes, and L. John Schreiner, "Evaluation of an Automated Seed Loader for Seed Calibration in Prostate Brachytherapy", Journal of Applied Medical Physics, Winter 2006, pp. 115-125, vol. 7, No. 1.

(Continued)

*Primary Examiner* — Charles A Marmor, II
*Assistant Examiner* — Carrie R Dorna
(74) *Attorney, Agent, or Firm* — Mendelsohn, Drucker & Dunleavy, P.C.

(57) ABSTRACT

A point-of-care seed stranding device for automating assembly of brachytherapy seed strands for implantation in patients. The device includes a number of features to reduce the potential for mistakes by the user, as well as to reduce the potential for damaging the radioactive seeds during the stranding process. Tactile feedback may be provided to prevent exertion of too much force in the packing step of the stranding process, as well as to indicate that the seed and/or strand cartridges are empty and need to be replaced. The device may also include a mechanism for holding seeds or spacers in place to allow automated packing of seeds or spacers having corresponding geometries. The device may also be provided with a seed counter which can be employed to preset the number of seeds in a strand and which disables the device from dispensing or packing additional seeds once the preset number of seeds has been packed into the strand. Also, methods for automated assembly of seed strands including the steps of setting the number of seeds, dispensing seeds and spacers, packing seeds and spacers and transferring assembled strands to another device.

21 Claims, 27 Drawing Sheets

(56) References Cited

U.S. PATENT DOCUMENTS

| | | | |
|---|---|---|---|
| 4,759,345 A | 7/1988 | Mistry | |
| 4,763,642 A | 8/1988 | Horowitz | |
| 4,784,116 A | 11/1988 | Russell et al. | |
| 4,815,449 A | 3/1989 | Horowitz | |
| 5,242,373 A | 9/1993 | Scott et al. | |
| 5,860,909 A | 1/1999 | Mick et al. | |
| 5,906,574 A | 5/1999 | Kan | |
| 6,010,446 A | 1/2000 | Grimm | |
| 6,221,003 B1 | 4/2001 | Sierocuk et al. | |
| 6,261,219 B1 * | 7/2001 | Meloul et al. | 600/3 |
| 6,273,851 B1 * | 8/2001 | Slater et al. | 600/8 |
| 6,530,875 B1 | 3/2003 | Taylor et al. | |
| 6,537,192 B1 | 3/2003 | Elliott et al. | |
| 6,585,633 B2 | 7/2003 | Vitali et al. | |
| 6,761,680 B2 | 7/2004 | Terwilliger et al. | |
| 6,969,344 B2 | 11/2005 | Drobnik et al. | |
| 2002/0077521 A1 | 6/2002 | Green et al. | |
| 2008/0004481 A1 * | 1/2008 | Bax et al. | 600/7 |
| 2008/0161635 A1 * | 7/2008 | Watson et al. | 600/7 |
| 2009/0105518 A1 | 4/2009 | Schreiber et al. | |

OTHER PUBLICATIONS

C.R. Bard, Inc, "Quick Link Delivery System", 1997-2007, p. 1, Published @ http://www.crbard.com/news/innovations/QuickLink.cfm.

* cited by examiner

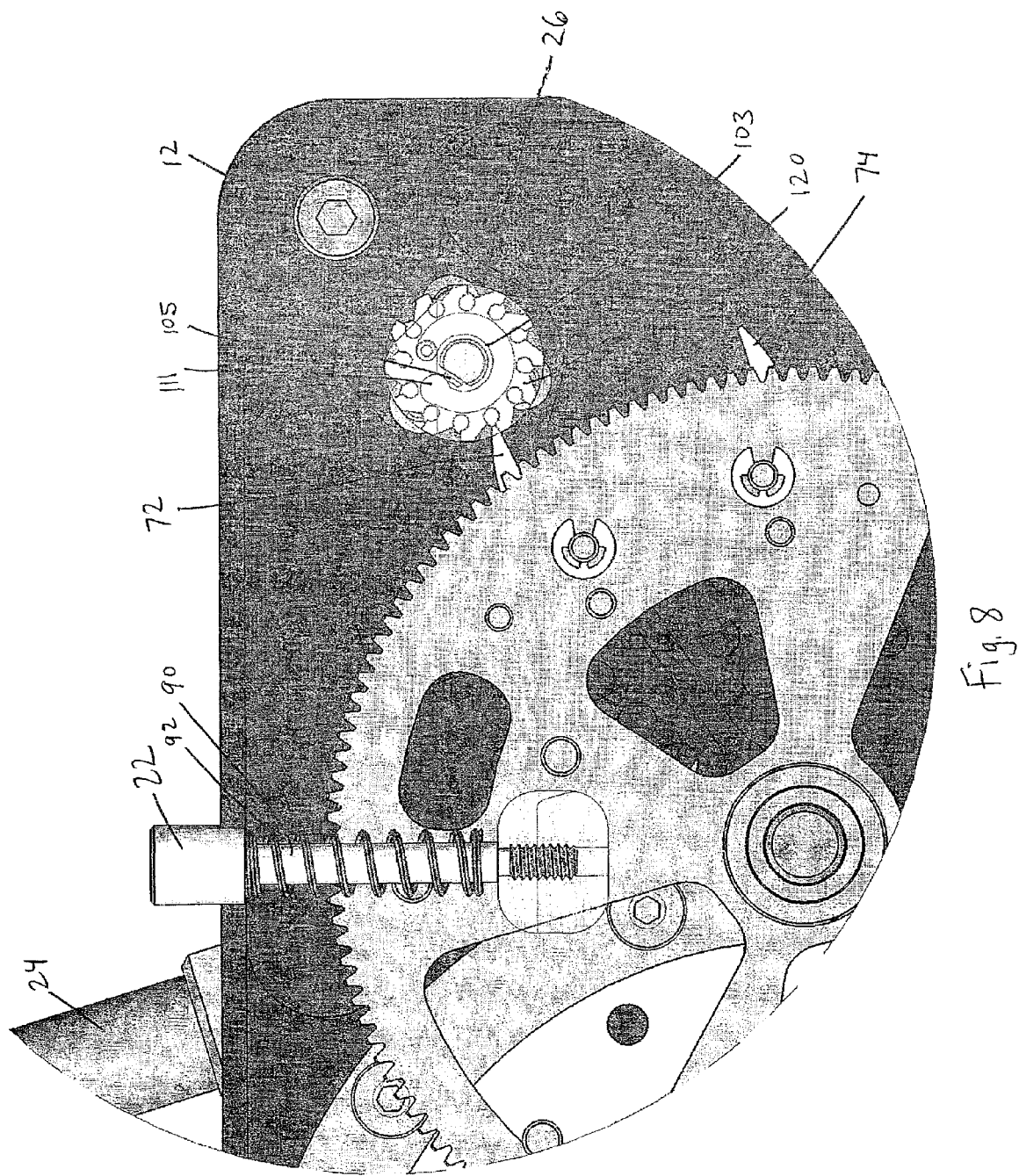

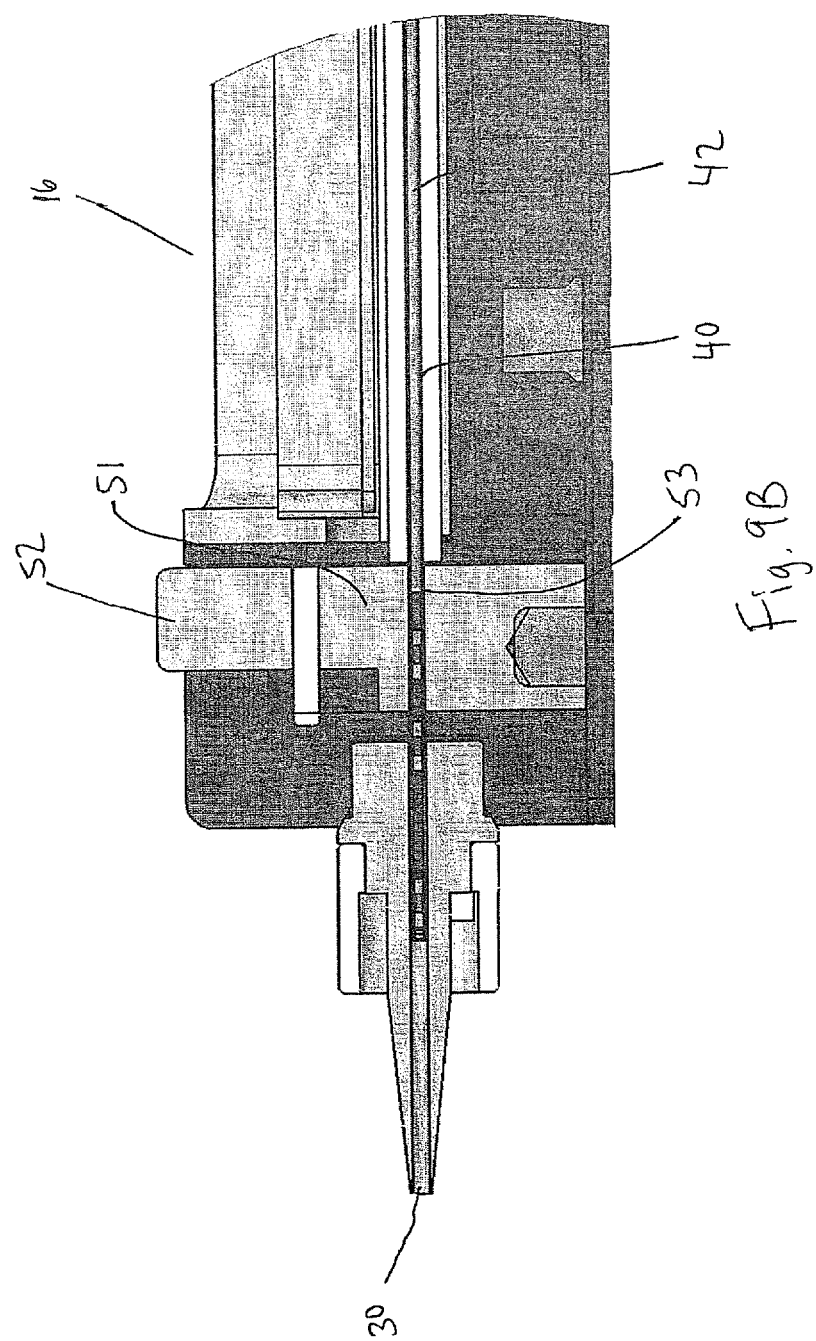

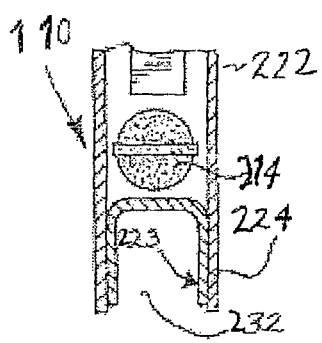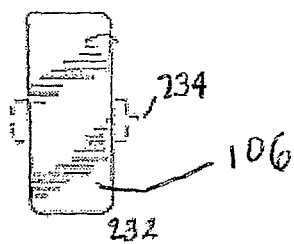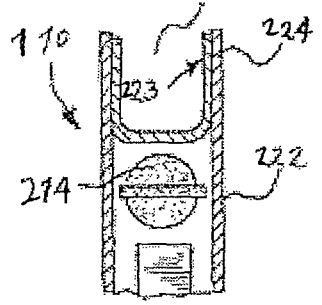
Fig. 13

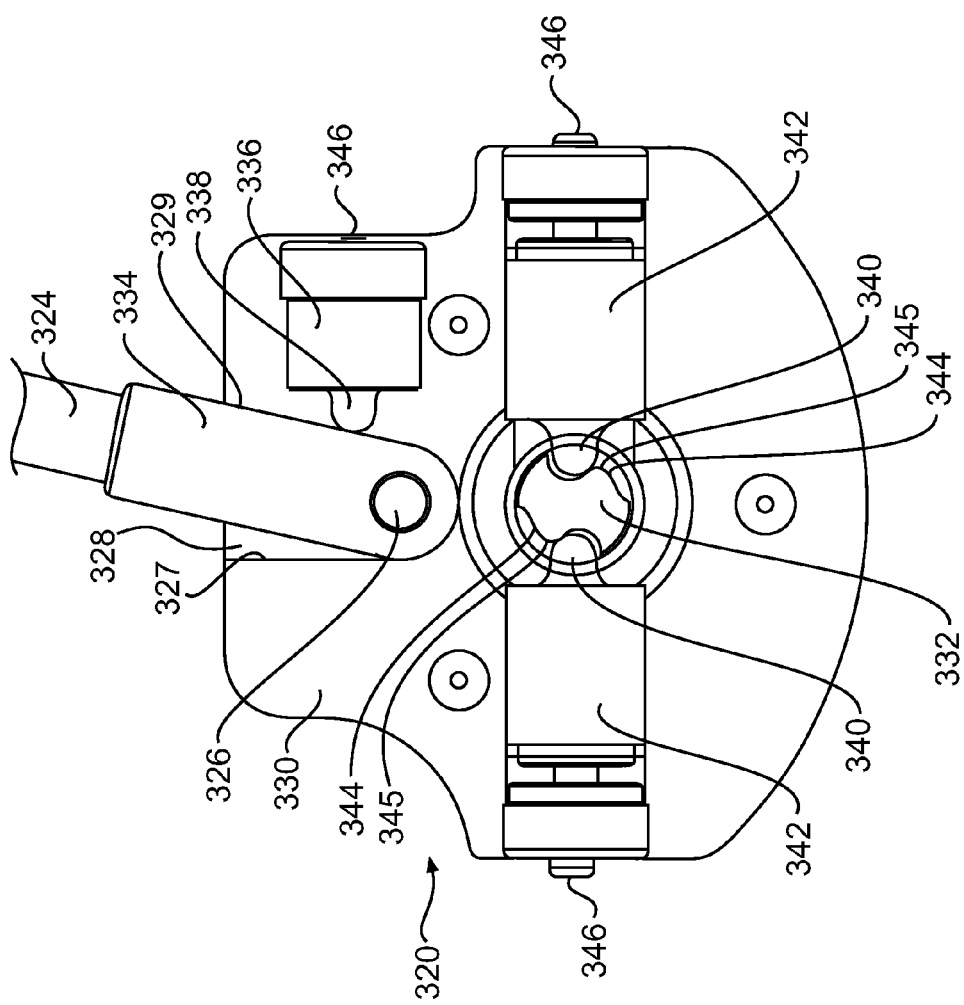

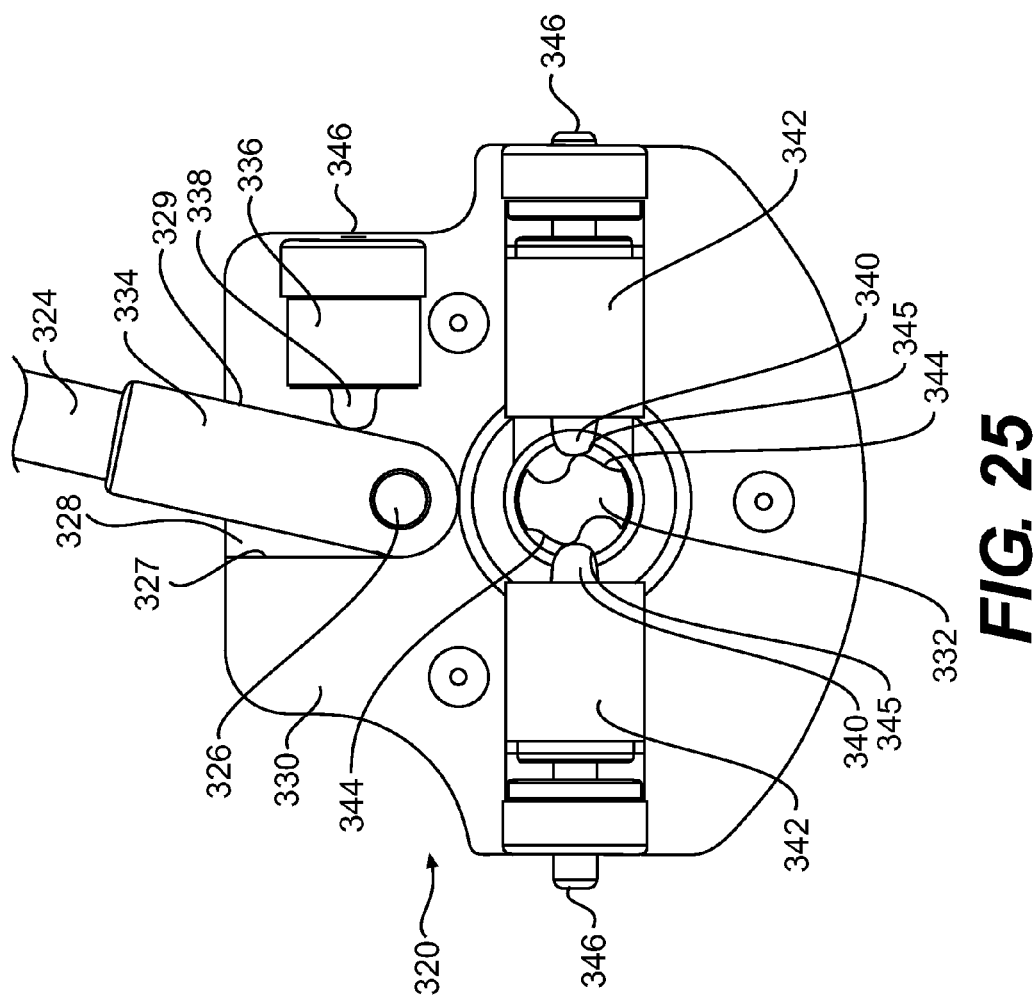

POINT OF CARE RADIOACTIVE MATERIAL STRANDING SYSTEMS

FIELD OF THE INVENTION

The present invention relates generally to medical devices for handling therapeutic radioactive materials. More specifically, the present invention relates to a point of care system for preparing strands of radioactive material for use in brachytherapy or other procedures.

BACKGROUND OF THE INVENTION

Radioisotopes are used in a variety of medical procedures. Some radioisotopes, typically characterized by one or more of short half-life, relatively shallow penetration depth and relative low radiation strength, are permanently implanted in a patient. Such radioisotopes are generally implanted using one or more implant needles with the radioisotopes encapsulated in small containers often referred to as seeds. In a typical procedure, a plurality of seeds are loaded into a plurality of implant needles and then ejected from the implant needle into the patient to form a three-dimensional array of seeds in a treatment area. Usually, the seed array is designed based on a pre-determined dose plan made by a medical professional.

In order to position the seeds at appropriate locations in the seed array, it is desirable to space the seeds apart from one another in the implant needles in order to provide appropriate spacing of the seeds in the treatment area. Thus, in a prostate cancer treatment method, 1-12 seeds are typically loaded into each implant needle along with a plurality of spacers to provide the desired spacing between seeds. It is preferable to allow customization of the number and/or length of spacers between seeds to provide greater flexibility in dose planning by allowing a larger variety of different spacing between seeds.

The loaded implant needles are positioned for insertion into the patient, for example, using a stand with an X-Y coordinate grid, and then inserted into the patient. The seeds and spacers are then ejected from the needle using a stylet as the needle is withdrawn from the patient in order to position the seeds at the desired location in the patient.

U.S. Pat. Nos. 4,086,914; 4,167,179; 5,242,373 and 5,860,909 and International application publication no. WO 97/22379 describe manual seed injector arrangements for brachytherapy using seed cartridges to supply the seeds directly to an implant needle specially adapted to mate with such cartridges or magazines.

Manual loading of implant needles just prior to insertion into a patient is undesirable for a variety of reasons. It is desirable to minimize potential exposure of hospital personnel to radioisotopes and thus manual loading of a large number of seeds at the time of treatment is undesirable. On the other hand, manual loading has the advantage that it provides more flexibility to the user to modify the dose plan at the time of implantation in order to provide the best possible treatment procedure for the patient and most economically efficient procedure for a hospital.

Some devices have been developed for loading seeds into implant needles. For example, U.S. Pat. No. 4,759,345 describes a radiation shielded seed loader for loading hand-implanted hypodermic needles. U.S. Pat. No. 5,906,574 describes a vacuum-assisted apparatus for loading radioactive seeds within a shielded container. U.S. Patent application publication no.: US 2002/0077521 A1 discloses methods and apparatus for loading radioactive seeds into brachytherapy needles. However, these devices require relatively difficult manipulations which may be time-consuming and may lead to inefficiency U.S. Pat. Nos. 4,815,449; 4,763,642 and 6,585,633 relate to seed carriers for pre-positioning and encasing a series of seeds into a bioabsorbable material for implantation in a patient.

U.S. Pat. Nos. 4,784,116; 6,010,446 and 6,969,344 disclose specialized designs of seeds and spacers for use in providing strands of seeds spaced apart from one another by spacers. Many commercially available seeds and spacers employ one or more of these specialized designs wherein one or both of the radioactive seeds and spacers are provided with specially shaped ends adapted to mate with one another. These seed and spacer designs provide for more structurally stable seed strands, once the strands have been assembled. However, the existence of these special designs presents additional challenges in the automation of the stranding process. For example, the spacers and strands must be held for positioning and accurately aligned by the automatic stranding device for the ends to properly mate with one another when the seed and spacer are pushed together by the device.

U.S. Pat. No. 6,537,192 relates to an automated radioisotope seed loader system for implant needles. The device includes a loading station adapted to receive a replaceable cartridge preloaded with a plurality of radioactive seeds and a plurality of spacers. Seeds and spacers can be selectively ejected from the cartridge into each of a plurality of implant needles. The system may also include a computer processor as a user interface to direct operation of the loading system to load a plurality of implant needles in accordance with a pre-determined dose plan.

Despite the existence of various devices for manual and automatic loading of implant needles, manual loading remains a cumbersome process that can result in undesirable exposure of users and other hospital personnel to unshielded radioisotopes. In addition, the automatic loading systems of the prior art suffer from disadvantages in allowing real-time loading in the operating room with the attendant flexibility to provide real-time treatment planning to the user during the procedure. Accordingly, it would be advantageous to provide a system for loading implant needles which would overcome one or more of these problems while improving one or more of the efficiency, flexibility and accuracy of the seed loading process.

SUMMARY OF THE INVENTION

The present invention relates to a seed stranding device which assembles and/or loads radioactive seed strands into a needle. The device includes a seed reservoir, a spacer reservoir, apparatus for indicating the number of seeds in a particular strand and apparatus for mechanically assembling and/or loading the strand. The design of the device is such that the device can automatically assemble seeds and spacers with mating geometry.

In another aspect, the present invention relates to methods for assembling and/or loading radioactive seed strands. In the method, seeds and spacers are selectively assembled to form customized seed strands in an efficient and reliable manner.

In a further aspect, the present invention relates to seed and/or spacer magazines for use in storing and dispensing of radioactive seeds and spacers. The seed and/or spacer magazines may be specially adapted for use with the seed-stranding device of the present invention to provide increased efficiency and/or reliability in the process of assembling seed strands using seeds and spacers dispensed from such magazines.

In a further aspect, the present invention relates to transfer barrels which may be used in conjunction with the strand assembly device of the present invention.

BRIEF DESCRIPTION OF THE DRAWINGS

FIG. 8 is a perspective view of the device from the reverse side with the housing removed showing the parts in the dispense position with the seed count indicator decremented to one.

FIG. 9B is a cross sectional view of the strand assembly section during the transfer step.

FIG. 13 is a view of an example of two seeds and a spacer that can be packed into a strand using the device of the present invention.

FIG. 24 is a front view of the torque handle assembly of FIG. 22 in the pack position showing the function of the tactile feedback mechanism, with a transparent housing to show internal parts thereof.

FIG. 25 is a front view of the torque handle assembly of FIG. 22 in the clutch-slip position which would be achieved by over-exertion of force on the torque handle assembly by the user, with a transparent housing to show internal parts thereof.

DETAILED DESCRIPTION OF THE PREFERRED EMBODIMENTS

In a first aspect, the present invention relates to a device for assembling seed strands and/or loading of seed strands into needles for placement in a patient as part of a brachytherapy treatment regimen. A perspective view of a seed-stranding device in accordance with one aspect of the present invention is shown in FIG. 1.

Figure 1A:
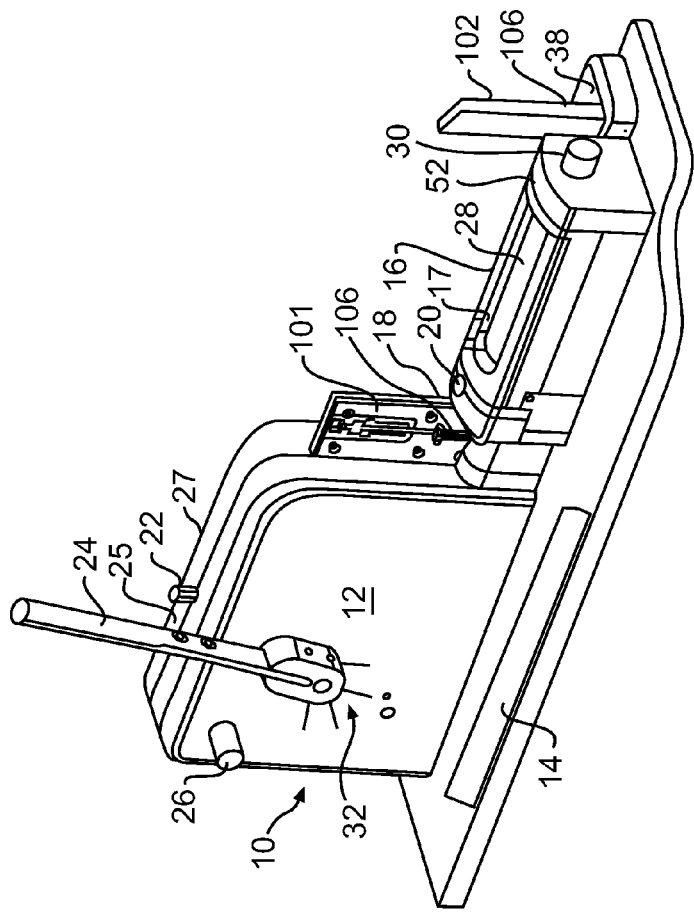
FIG. 1A is a perspective view of one embodiment of a seed stranding device in accordance with the present invention.

Referring to FIG. 1, seed stranding device 10 includes a housing 12, a base 14, a strand assembly section 16, a spacer cartridge dock 18 and a seed cartridge dock 20. Seed stranding device 10 is designed to rest on a horizontal surface and may be portable so that it can be transported to a desired location for use. Base 14 allows device 10 to rest stably on a horizontal surface and facilitates transport of device 10 to different locations. In use, device 10 may be located in the same room where the brachytherapy procedure will take place to allow assembly and/or loading of the seeds or seed strands at the time and location of the brachytherapy treatment. This provides maximum flexibility to the user since treatment planning can be adjusted based on the latest information or feedback from the brachytherapy procedure itself.

Housing 12 may house apparatus used for selecting and dispensing seeds and spacers, apparatus for providing visual and tactile feedback to the user, as well as apparatus for holding and positioning seeds and spacers for assembly of seed strands. Shown on housing 12 in FIG. 1 are a lock release button 22, a handle 24 and a seed count indicator 26, the function of each of which is explained in detail below.

Strand assembly section 16 includes a viewing area 28 which may be provided with a transparent cover 17 to allow viewing of the strand by the user as the strand is assembled by device 10. In use, device 10 assembles seed strands in viewing area 28 of strand assembly section 16. Strand assembly section 16 is also provided with a strand outlet 30 through which assembled strands may be transferred from strand assembly section 16 to another apparatus. In various embodiments of the methods of the invention, it is contemplated that an implantation needle or a transfer barrel may be attached to, or associated with, strand outlet 30 to allow assembled strands to be transferred from strand assembly section 16 directly into the implantation needle or transfer barrel.

Figure 10:
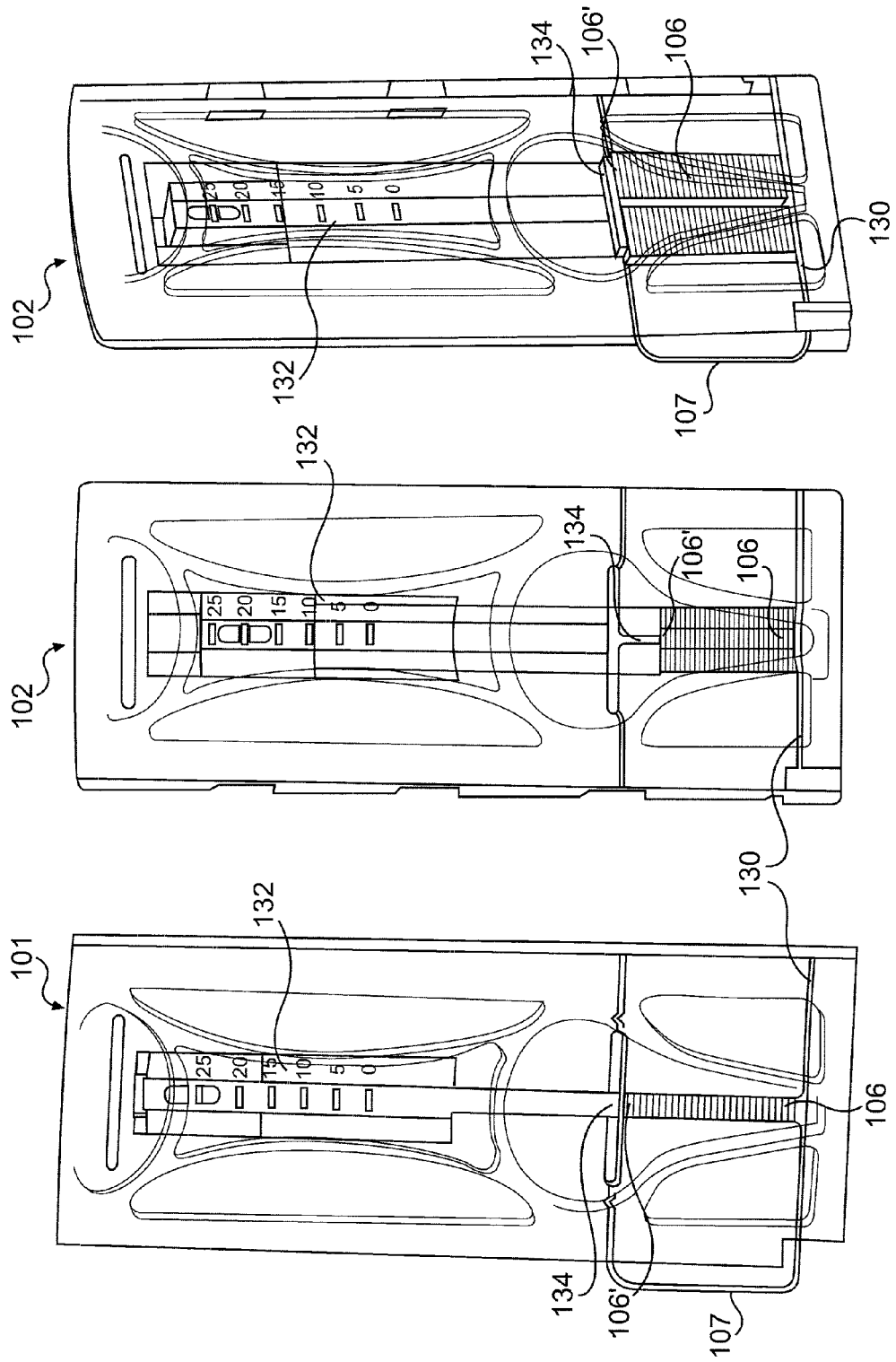
FIG. 10 is a view of three semi-transparent spacer cartridges for use in the present invention.

Spacer cartridge dock 18 is designed to receive a spacer cartridge 101, 102 which contains a plurality of spacers 106 therein. Spacer cartridge dock 18 may be specially adapted for receiving a variety of different types of spacer cartridges 101, 102. Referring to FIG. 10, spacers 106 are typically dispensed from spacer cartridges 101, 102 via a spacer channel 130. In the start position of handle 24, a single spacer 106 falls into, or is positioned in, spacer channel 130 and is concentrically aligned with spacer channel 130. Stylet 42 is then pushed through spacer channel 130 to push spacer 106 out of spacer channel 130 and thereby out of spacer cartridge 101, 102 by, for example, moving handle 24 from the start position to the dispense position. Pushing seeds and spacers out of seed and spacer cartridges using a stylet is a conventional method for dispensing seeds and spacers from seed or spacer cartridges. In device 10 of the present invention, spacer cartridge dock 18 ensures that spacer channel 130 of spacer cartridge 101, 102 is aligned with stylet channel 40 so that stylet 42 can pass through spacer channel 130 of spacer cartridge 101, 102 during the dispensing, packing and transfer steps. Once a spacer 106 is pushed out from spacer cartridge 101, 102 during the dispensing step, stylet 42 takes the place of spacer 106 in spacer channel 130 of spacer cartridge 101, 102. As a result, it is not possible for another spacer 106 to fall into spacer channel 130 until stylet 42 is removed from spacer channel 130 by returning handle 24 to the start position. Once stylet 42 is retracted by returning handle 24 to the start position, another spacer 106 falls into or is positioned in spacer channel 130 for the next dispensing step. Spacer cartridges 101, 102 may include a visual indicator 132 that shows how many spacers 106 remain in spacer cartridge 101.

Spacer cartridges 101, 102 may be provided with a spacer stop clip 107 which engages with spring-loaded bar 134 during storage and transport of spacer cartridges 101, 102 prior to use in order to minimize or prevent exertion of force on spacers 106 by spring-loaded bar 134 until this is needed for dispensing. The user removes spacer stop clip 107 from spacer cartridges 101, 102 prior to use to thereby allow spring-loaded bar 134 to push down on spacers 106. Spacer stop clip 107 prevents mechanical distortion or the sticking together of spacers 106 which could otherwise be caused by long periods of force being exerted on spacers 106 by spring-loaded bar 134 during storage and transport of spacer cartridges 101, 102.

To ensure proper dispensing of spacers 106 from spacer cartridges 101, 102, a pushing mechanism may be provided as part of spacer cartridge 101, 102 to push down on spacers 106 and ensure that spacers 106 drop into spacer channel 130 each time the previous spacer 106 has been pushed out of spacer cartridge 101, 102. Thus, for example, as a suitable pusher mechanism, spacer cartridges 101, 102 may include a spring-loaded bar 134 which pushes downwardly on topmost spacer 106' as a result of spring loading on spring-loaded bar 134. Spring-loaded bar 134 may perform another important function in the device 10 of the present invention since, when all spacers 106 have been dispensed from spacer cartridge 101, 102, spring-loaded bar 134 may be used to block spacer channel 130 in spacer cartridge 101, 102. This is useful since stylet 42 will abut against spring-loaded bar 134 when spacer cartridge 101, 102 is empty, thereby preventing handle 24 from moving from the start position to the dispense position. This provides immediate tactile feedback to the user indicating that spacer cartridge 101, 102 is empty and also prevents dispensing of a seed 110 without the associated spacer 106 therewith. This can be used as a fail-safe mechanism to prevent the user from forgetting a spacer 106 in the strand if the user does not monitor visual indicator 132 of spacer cartridge 101, 102 and know that a spacer cartridge 101, 102 is empty.

Figure 1B:
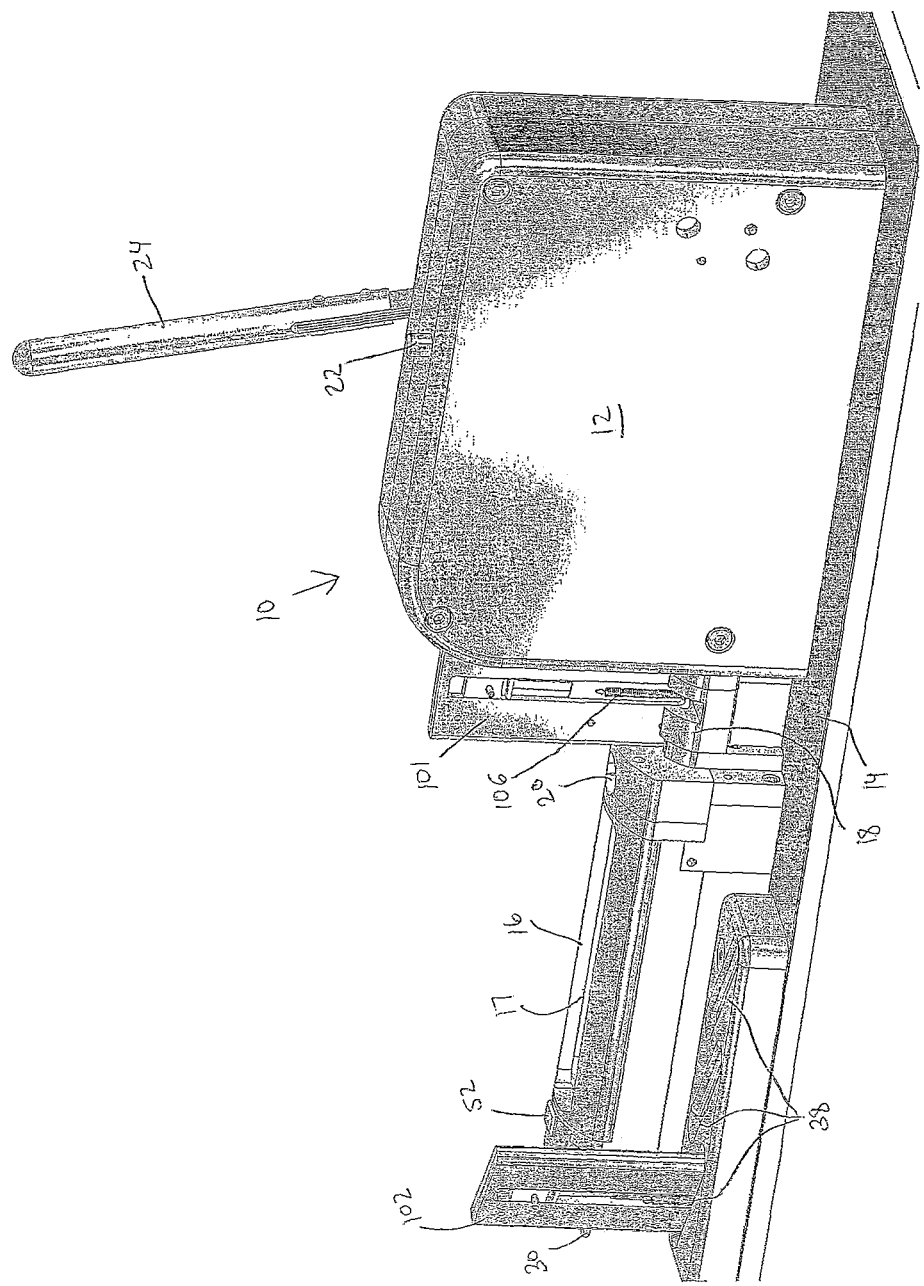
FIG. 1B is a perspective view of the seed stranding device of FIG. 1A from the opposite side.

Device 10 may be provided with a plurality of spacer cartridges 101, 102. As shown in FIG. 1B, device 10 is provided with one spacer cartridge dock 18 and three additional spacer cartridge holders 38. Additional spacer cartridges 101, 102 may be stored in spacer cartridge holders 38. This permits device 10 to have associated with it for use by the user, four different lengths of spacers 106 at the same time such that the user can select particular length spacers to achieve a desired spacing between radioactive seeds in the assembled seed strands. The user may selectively dock a desired spacer cartridge 101, 102 with spacer cartridge dock 18 to selectively dispense spacers 106 from each of the spacer cartridges 101, 102 for use in assembly of a seed strand. Spacer cartridges 101, 102 may also be referred to as spacer magazines and thus references to spacer cartridges 101, 102 herein also refer to spacer magazines. Any suitable means 38 for holding or retaining additional spacer cartridges 101, 102 may be included as part of device 10 or associated with device 10 to provide treatment planning flexibility to the user.

Seed cartridge dock 20 is designed to receive a seed cartridge 108 therein for dispensing seeds into position for assembly into the seed strand. Seed cartridge dock 20 may be specially adapted to accept different variations of conventional seed cartridges, as well as to employ the seed cartridge 108 of the present invention that is described in greater detail below. Seed cartridges are also sometimes referred to as seed magazines and thus all references to seed cartridges herein also refer to seed magazines.

Figure 11:
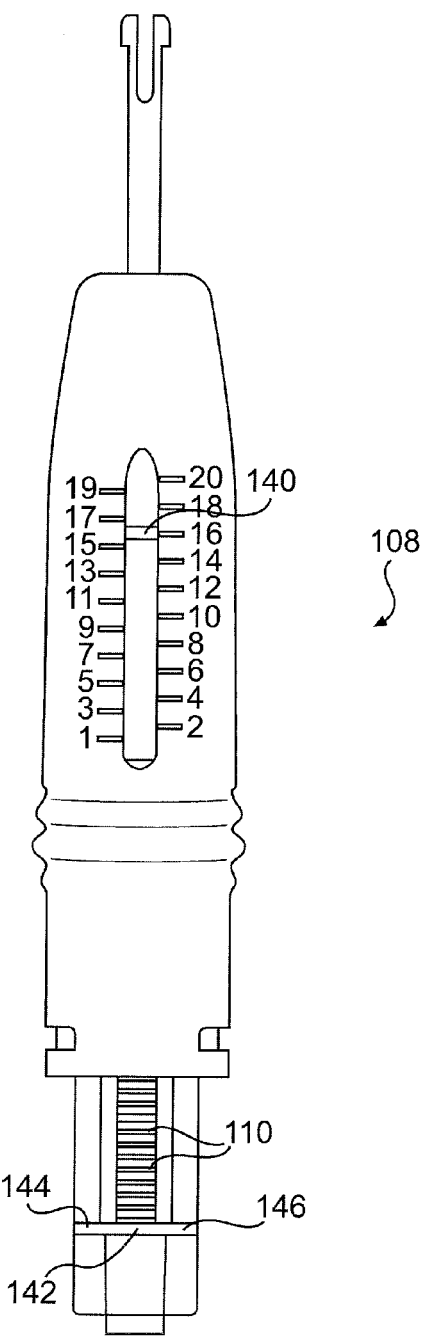
FIG. 11 is a front view of a specially adapted seed cartridge for use in the present invention.
Figure 12:
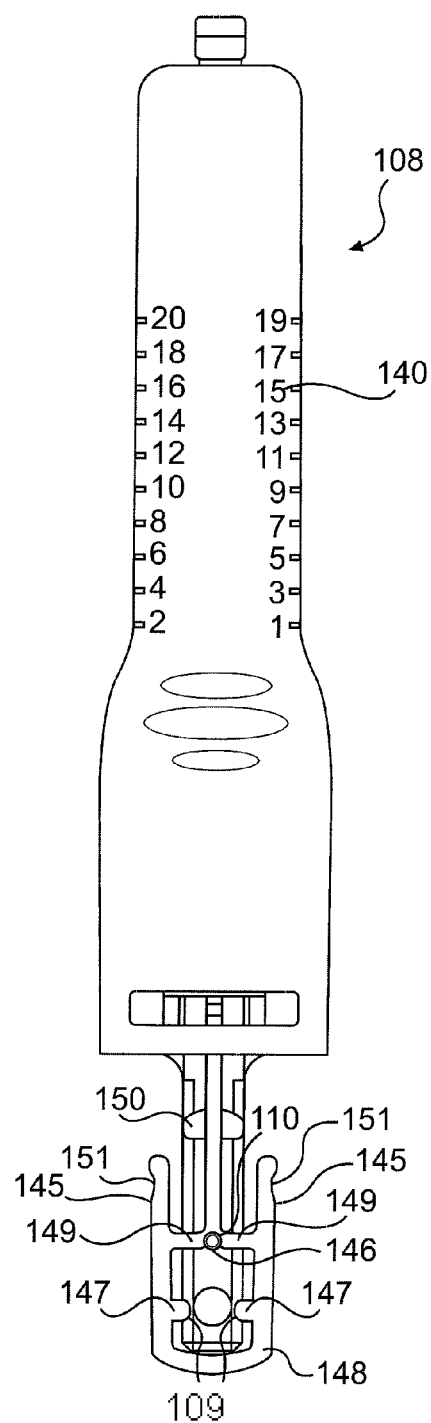
FIG. 12 is a side view of the seed cartridge shown in FIG. 11.

A specially adapted seed cartridge 108 for use in the present invention is shown in greater detail in FIGS. 11-12. Referring to FIG. 11, seed cartridge 108 includes a seed indicator 140 for indicating the number of seeds remaining in seed cartridge 108. A plurality of seeds 110 is housed in seed cartridge 108. Seed cartridge 108 includes a seed channel 142 which passes completely through seed cartridge 108. Seed channel 142 is specially adapted for use in device 10 of the present invention since seed channel inlet portion 144 is of a smaller diameter than seed channel outlet portion 146. This is a particularly useful feature of seed cartridge 108 since seed channel inlet portion 144 functions to concentrically align an incoming spacer 106 with an end cup of a seed 110 located in seed channel 142. This is beneficial since proper alignment of spacers 106 and seeds 110 are required to properly pack spacers 106 with seeds 110 by fitting a smaller diameter leading end of spacer 106 into a suitable sized end cup of seed 110. In an exemplary embodiment, stylet 42 may have a diameter of 0.023 inches (0.0584 cm), seed channel inlet 144 may have a diameter of 0.025 inches (0.0635 cm), which is just large enough to accommodate spacers 106 of the same diameter. Seeds 110 of the type described in FIG. 13 may have a diameter of 0.032 inches (0.0813 cm) and seed channel outlet portion 146 may have, for example, a diameter of 0.035 inches (0.0889 cm.

FIG. 12 shows the flexible locking clip 148 that includes fingers 149 for grasping seed 110 when flexible locking clip 148 is actuated to the lock position shown in FIG. 12. Also shown in FIG. 12 is the seed plunger 150 that is biased downwardly to push against seeds 110 in seed cartridge 108 and force the seeds 110 downward to ensure that a seed 110 is positioned in seed channel 142 for dispensing. Flexible locking clip 148 snaps onto seed cartridge 108 by virtue of fingers 147 which fit into corresponding indentations 109 in seed cartridge 108.

FIG. 13 shows an example of two seeds 110 and a spacer 106 which can be employed to make strands using device 10 of the present invention. Spacer 106 is adapted to join seeds 110 in an end-to-end relationship. Spacer 106 is dimensioned to fit within the end cups 232 formed in the interior of outwardly extending end caps 223. Spacers 106 are preferably cylindrical in configuration having an outside diameter sized for significant frictional engagement with end cups 232 of seeds 110. Spacers 106 may have other geometries as long as they effectively engage end cups 232 of seeds 110. For example, spacers 106 could be provided with ribs 234 around the circumference of the spacers 106 which are of sufficient diameter to frictionally engage end cups 232 of seeds 110. Also, spacers 106 may have the same largest outside diameter as the largest outside diameter of seeds 110 and be provided with reduced diameter end portions, not shown, which frictionally engage end cups 232 of seeds 110.

Seeds 110 preferably include a radioactive material 214 therein. Radioactive material 214 is housed in an annular container formed by annular walls 222, 224.

Proper packing of spacers 106 into end cups 232 of seeds 110 ensures proper spacing of seeds 110 in the assembled strand by ensuring that the spacers 106 fit snugly within end cups 232 of end caps 223 of seeds 110 such that the spacing distance provided by packed spacers 106 is consistent from seed to seed. Seed channel outlet portion 146 has a larger diameter than seed channel inlet portion 144 to accommodate the larger diameter seed 110 as the packed combination of spacer 106 and seed 110 are pushed out of seed cartridge 108 through seed channel outlet portion by stylet 42 during the dispensing step and into strand assembly section 16. This simple mechanism also ensures that the leading end of a second or subsequent seed 110 in a strand is concentrically aligned with the trailing end of the previous spacer 106 that has already been dispensed into the strand assembly section 16. Stylet channel 40 is of a diameter close enough to the outside diameter of seeds 110 to position seeds 110 within stylet channel 40 in strand assembly section 16. Since spacers 106 are packed into end caps 223 of seeds 110, their smaller diameter does not create an alignment problem because end caps 223 of seeds 110 hold packed spacers 106 in the proper position to mate with end caps 223 of the next seeds 110 in the strand when they are pushed against spacer 106 during the packing step.

In order to ensure proper engagement of spacer 106 within end cap 223 of seed 110, it is desirable to hold seed 110 in position while spacer 106 is pushed into end cap 223 during the dispensing step. A suitable mechanism for holding seeds 110 during the dispensing step is described in greater detail below with reference to FIGS. 14-18.

Handle 24 may be moved to several different positions to actuate various aspects of device 10. Each of these positions is indicated by handle position label 32 located on housing 12. As can be seen from FIG. 1, handle 24 may be moved to any one of four different positions: start, dispense, pack and transfer. The start position is used when initiating assembly of a new strand, as well as between each dispensing step. The dispense position is used when dispensing seeds or spacers for use in assembling a strand. The pack position is used when packing dispensed seeds or spacers into an assembled strand. The transfer position is used to transfer an assembled strand from strand assembly section 16 to another device via strand outlet 30.

One method of operation of device 10 will now be described to facilitate understanding of device 10. Initially, a selected spacer cartridge 101, 102 is docked with spacer cartridge dock 18 and a seed cartridge 108 is docked with seed cartridge dock 20. Then, device 10 is ready for use to assemble a seed strand.

To initiate assembly, handle 24 is positioned in the start position. While handle 24 is in the start position, the user selects the number of seeds that are to be assembled into that particular strand using seed count indicator 26. Thus, if seven seeds are desired for a particular strand, seed count indicator 26 is set to the number 7 with handle 24 located in the start position. This provides the user with the flexibility to customize the number of seeds used in each assembled strand at the time of strand assembly and also allows the strand assembly device 10 to prevent the user from accidentally dispensing too many seeds into a particular strand. Seed count indicator 26 can also be used to ensure that the initially selected number of seeds must be assembled into the seed strand before the strand can be transferred out of the seed strand assembly device. It is possible for the user to add additional seeds to the number of seeds initially selected for a particular seed strand or to reduce the number of seeds initially selected for a particular seed strand during the process of strand assembly since it remains possible to increment or decrement seed count indicator 26 to add additional seeds or reduce the number of seeds in a particular strand, when handle 24 is positioned in the start position between each dispensing step. Once seed count indicator 26 decrements to one it is no longer possible to move handle 24 to the start position without the handle first traveling through the pack and transfer positions. This functions as a fail-safe mechanism to prevent the user from assembling more than the desired number of seeds into a particular seed strand before transferring the strand out of the device.

Figure 2:
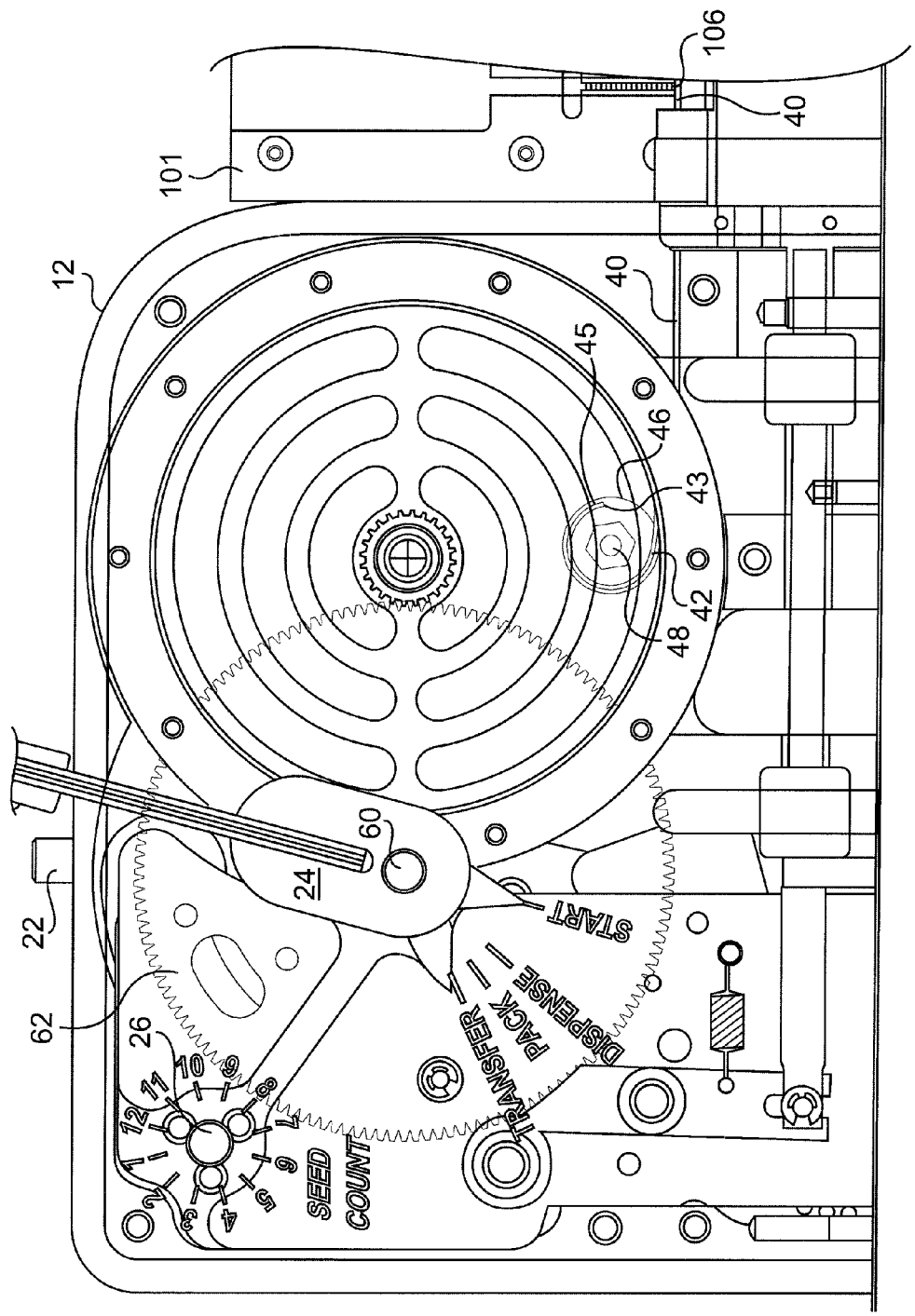
FIG. 2 is a view of the device of FIGS. 1A-1B in the start position with the housing removed to show additional parts of the device.

A seed 110 and a spacer 106 are positioned in a stylet channel 40, as shown in FIG. 2, when seed and spacer cartridges 108 and 101, 102 are docked with seed and spacer cartridge docks 18, 20 and handle 24 is in the start position. The user may select a spacer 106 for dispensing by docking a particular spacer cartridge 101, 102 with the spacer cartridge dock 18. Different length spacers 106 can be housed in different spacer cartridges 101, 102 for this purpose.

The next step in the process is the dispense step, which dispenses a spacer 106 and seed 110, engages an end of spacer 106 with an end cup 232 of seed 110 and moves the engaged spacer 106 and seed 110 pair into the strand assembly section 16. In order to carry out this step, the user moves handle 24 from the start position to the dispense position. When handle 24 is moved from the start position to the dispense position, stylet 42 is caused to travel along stylet channel 40 through spacer cartridge 101 and seed cartridge 108. As it moves, stylet 42 pushes spacer 106 out of spacer cartridge magazine 101 and up against a seed 110 located in seed cartridge 108. When spacer 106 abuts seed 110, spacer 106 is caused to mechanically engage with seed 110 to form an engaged pair including a spacer 106 and a seed 110. The engagement of spacer 106 and seed 110 is facilitated by a seed holding mechanism, an example of which is described in reference to FIGS. 14-18 below. The engaged pair of spacer 106 and seed 110 is then pushed out of seed cartridge 108 and moved into strand assembly section 16.

Figure 7:
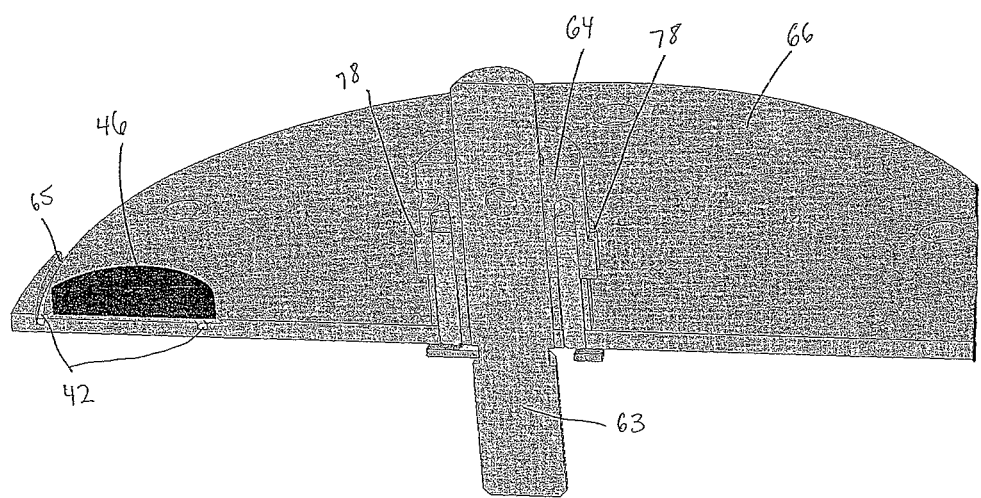
FIG. 7 is a cross-sectional view showing a portion of the assembly for advancing and retracting the stylet in response to movement of the handle.

The mechanism which advances stylet 42 along stylet channel 40 is shown in FIG. 7. Specifically, a circular plate 66 is mounted for rotational movement on stylet gear 64 which, in turn, is mounted on shaft 63. Rotation of handle 24 causes rotation of stylet gear 64 which, in turn, rotates circular plate 66. Circular plate 66 is provided with a v-shaped stylet groove 65 around the periphery of circular plate 66 in which stylet 42 is trapped such that rotation of circular plate 66 advances stylet 42 along stylet channel 40.

Once the dispensing step is completed, handle 24 is returned to the start position Returning handle 24 to the start position retracts stylet 42 along stylet channel 40 since stylet 42 to allow positioning of a new seed 110 and spacer 106 in stylet channel 40 for dispensing. Specifically, once stylet 42 is retracted, a seed 110 can fall into, or be positioned in, a position in seed cartridge 108 whereby seed 110 is located in stylet channel 40. Similarly, a spacer 106 can drop into, or be positioned in, a position in spacer cartridge 101 whereby spacer 106 is located in stylet channel 40. Moving handle 24 from the dispense position to the start position also decrements seed count indicator 26 by one to thereby indicate the remaining number of seeds 110 which are to be assembled into that particular strand.

If the desired spacer 106 is the same spacer 106 as was dispensed in the previous dispensing step, the user can proceed directly to the next dispense step to dispense a second engaged seed 110 and spacer 106 pair of the seed strand into strand assembly section 16. However, if a different length spacer is desired, spacer cartridge 101 can be disengaged from spacer cartridge dock 18 and the appropriate spacer cartridge 101, 102 containing a spacer 106 of a different length may then docked to spacer cartridge dock 18. This provides the user with the flexibility to customize the strand by selecting a different length spacer 106 for each dispensing step to thereby obtain variable spacing between seeds 110 in the assembled seed strand. Once the desired spacer 106 is positioned in stylet channel 40 by docking the correct spacer cartridge 101, 102 to spacer cartridge dock 18, the user may proceed to the dispensing step, as described above. The user then repeatedly moves handle 24 between the start and dispense positions to continue to dispense engaged pairs of spacers 106 and seeds 110 into strand assembly section 16 until seed count indicator 26 decrements to one.

Once seed count indicator 26 decrements to one, dispensing is complete. Optionally, device 10 may be configured to prevent movement of handle 24 to the start position when seed count indicator 26 is at one in order to prevent dispensing of more seeds 110 than were selected by the user for assembly into that particular strand. A mechanism that can prevent movement of handle 24 to the start position when seed count indicator 26 indicates one is shown in FIG. 8. More specifically, in FIG. 8 handle 24 is shown in the dispense position. To move handle 24 to the start position from the dispense position shown in FIG. 8 would require handle 24 to move to the right. However movement of handle 24 to the right is prevented when seed count indicator 26 is decremented to one since ratchet 74 hangs up on one of the teeth of toothed wheel 120 as shown in FIG. 8. Toothed wheel 120 includes a cam surface 103 that engages a cam follower 105. Cam surface 103 is provided with an enlarged end 111 which acts as a stop to prevent further rotation of cam surface 103 relative to cam follower 105 when seed count indicator indicates one.

Once seed count indicator 26 decrements to one, the user depresses lock release button 22 which releases a locking mechanism connected to handle 24 to permit handle 24 to be moved from the dispense position to the pack position. Stylet 42 is advanced to pack the engaged pairs of spacers 106 and seeds 110 tightly together against the resistance of mechanical stop 50 to form a strand in strand assembly area 16. Engaged pairs of spacers 106 and seeds 110 provided with mating structures may be mated together by exertion of a sufficient force on the trailing engaged pair of a spacer 106 and a seed 110. Also, increased resistance on handle 24 can be felt by the user to indicate that the packing step is complete. This can be, for example, a tactile stop that may be accompanied by an audible click. Also, the user may visually verify in the viewing area 28 that the packing step has been completed.

Handle 24 may be provided with a means to allow an upper portion of handle 24 to bend upon exertion of a predetermined amount of force on handle 24. Such a means may be, for example, a leaf spring 25 that will allow handle 24 to bend at joint 27 when a predetermined amount of force is exerted on handle 24. The purpose of this feature is to provide a mechanism to help ensure that during at least the packing step, and, optionally also the dispensing and transfer steps, seeds 110 and spacers 106 are not damaged by exertion of too much force thereon via action of handle 24. Thus, the force required to exceed the force of leaf spring 25 is selected to allow handle 24 to bend at a point where the force exerted on seeds 110 and spacers 106 does not to exceed a predetermined safe level in order to prevent damage to seeds 110 and spacers 106 during the packing, dispensing and/or transfer steps. This is particularly important to ensure that radioactive seeds 110 do not break and allow radioactive material to spread through the patient. Preferably, leaf spring 25 is adjustable to allow different levels of force to be set to accommodate packing, dispensing and/or transfer of different types of seeds and/or spacers. Device 10 may alternatively be provided with a radial spring, a coil spring, or any other suitable spring, or a clutch as another means to prevent exertion of too much force on seeds 110 and spacers 106 during the packing, dispensing and/or transfer steps. An alternative handle provided with a clutch is described in detail below with reference to FIGS. 19-23.

Figure 9A:
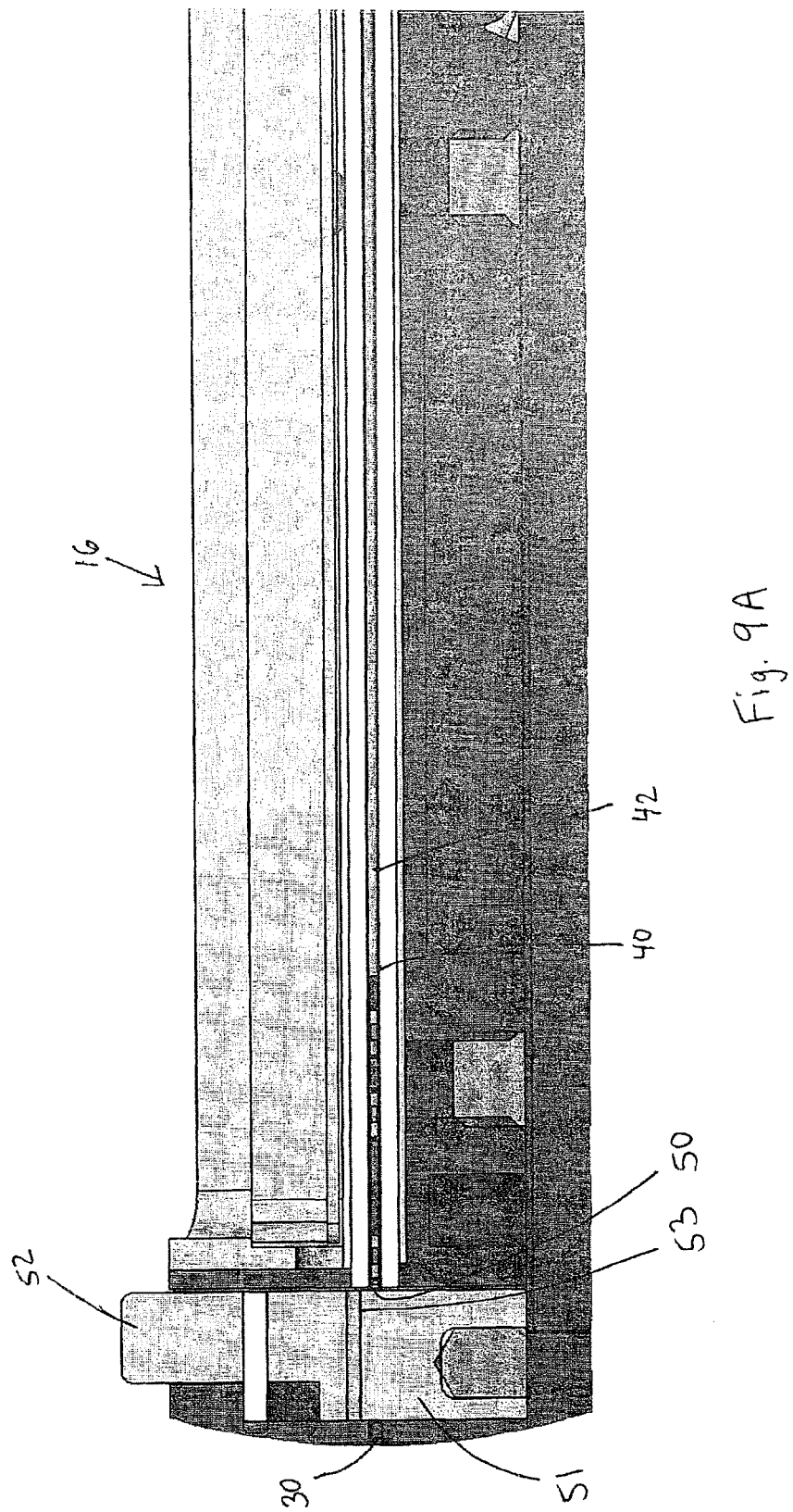
FIG. 9A is a cross sectional view of the strand assembly section during the packing step.

A transfer barrel or needle may be attached to strand outlet 30 to allow transfer of the packed strand from strand assembly section 16 to the transfer barrel or needle via strand outlet 30. When it is desired to transfer the completely assembled strand, the user depresses transfer button 52 to cause mechanical stop 50 to clear stylet channel 40 for transfer of the seed strand through strand outlet 30 out of strand assembly section 16. Referring to FIGS. 9A-9B, there is shown a cross-sectional view of strand assembly section 16. In FIG. 9A, transfer button 52 has not yet been depressed. As a result, pin 51 is in the position shown, with transfer channel 53 located out of alignment with stylet channel 40. In this position, which is maintained during the start, dispense and pack steps, a portion of pin 51 blocks stylet channel 40, as shown, thereby acting as a mechanical stop 50 which is used to resist the strand and allow packing of the strand by advancing stylet 42 in stylet channel 40. Depressing button 52 prior to the transfer step moves pin 51 downwardly to align transfer channel 53 with stylet channel 40 thereby allowing the assembled strand to be transferred from strand assembly section 16 to transfer outlet 30 via transfer channel 53, as shown in FIG. 9B. Once mechanical stop 50 is moved, it is possible to move handle 24 from the pack position to the transfer position.

Movement of handle 24 to the transfer position causes further advancement of stylet 42 in stylet channel 40 to push the assembled strand out of strand assembly section 16, via transfer channel 53 in pin 51 through strand outlet 30 and into a transfer barrel or needle. This is facilitated by the mechanism that translates a small movement of handle 24 to a larger movement of stylet 42. Sufficient travel distance may be provided for at least a portion of stylet 42 to protrude from strand outlet 30 to facilitate problem-free transfer of the strand.

Movement of handle 24 to the transfer position increments seed count indicator to 2 by engagement of ratchet 74 with toothed wheel 120 to move toothed wheel 120. Once the assembled strand has been transferred, handle 24 may be returned to the start position since seed count indicator is set to a value of 2, and thus will no longer prevent passage of ratchet 72. Return of handle 24 to the start position again decrements seed count indicator 26 to one or to a starting value and causes stylet 42 to be retracted from stylet channel 40. The device is then ready to assemble another seed strand in the same manner as described above.

Figure 3:
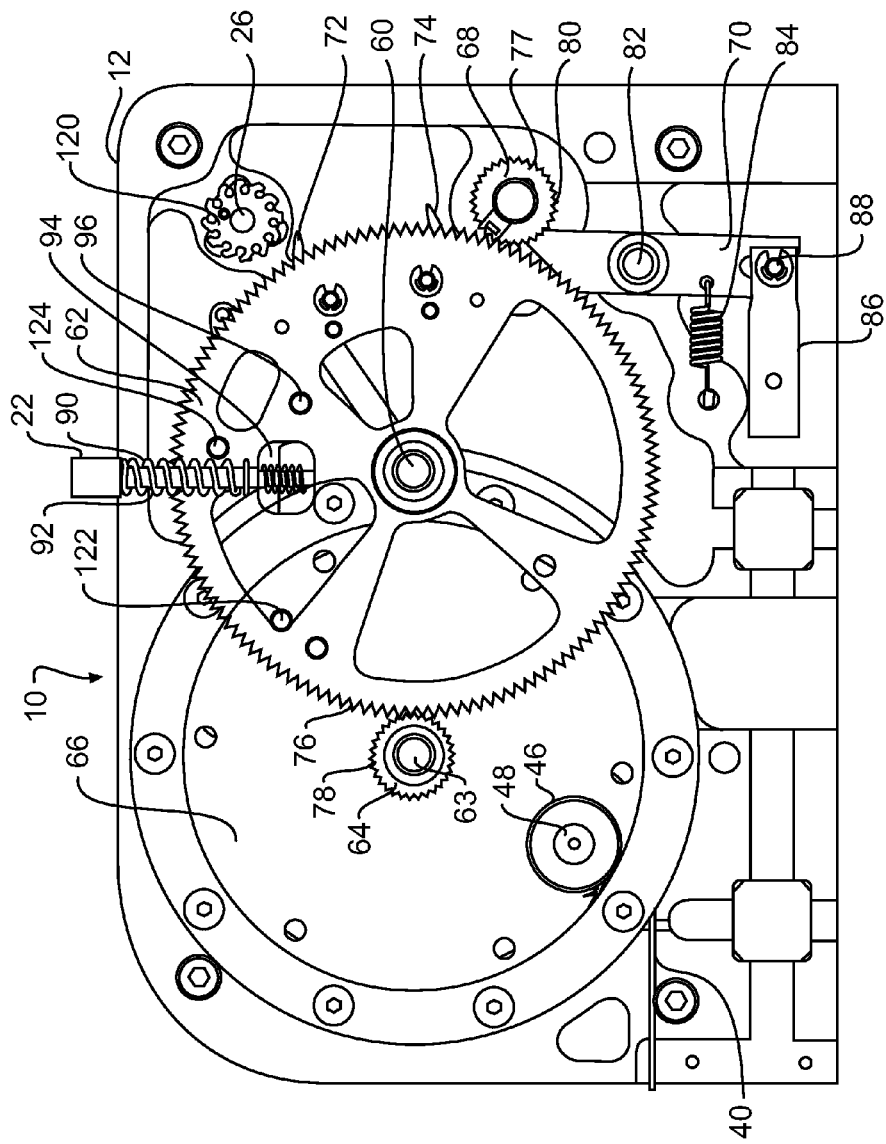
FIG. 3 is a view of the device of FIGS. 1A-2, from the reverse side with the housing removed showing the parts in the start position.

Referring now to FIGS. 3-6, the operation of device 10 will be described in greater detail. FIG. 3 shows device 10 with handle 24 in the start position. It can be seen from FIG. 2 that handle 24 is connected to gear wheel 62 by a connection 60 such that movement of handle 24 among its four positions is translated to rotational movement of gear wheel 62. From FIG. 3, it can be seen that gear wheel 62 interacts with stylet reel 46 via stylet gear 64 and circular plate 66, and that gear wheel 62 interacts with arm 70 via arm gear 68. In addition, gear wheel 62 is provided with two ratchets 72 and 74 connected to gear wheel 62 for decrementing and incrementing seed count indicator 26, respectively. As shown in FIGS. 3-6, movement of handle 24 in the direction from the start position towards the transfer position causes gear wheel 62 to rotate in a counter-clockwise direction, thereby causing circular plate 66 and arm gear 68 to rotate in a clockwise direction.

Thus, movement of handle 24 causes rotation of gear wheel 62. Rotation of gear wheel 62 causes rotation of stylet gear 64 since teeth 76 of gear wheel 62 engage teeth 78 of stylet gear 64. Stylet gear 64 is connected to circular plate 66 such that rotation of stylet gear 64 causes a corresponding rotation of circular plate 66 through an arc of the same number of degrees. In this manner, a relatively small movement of handle 24 is translated to a relatively large rotation of circular plate 66. Stylet reel 46 is mounted to circular plate 66, also shown in FIG. 7.

Device 10, as shown, allows assembly of seed strands of up to 7 cm in length. Thus, stylet 42 need only move about 16-26 cm to accomplish its function of moving spacers 106 and seeds 108 from their dispensing locations, through strand assembly section 16 and out through transfer outlet 30. As a result, each movement of handle 24, i.e. from the start position to the dispense position, from the dispense position to the pack position and from the pack position to the transfer position, is translated to a movement of the stylus 42 of about 6-9 cm by the combination of gear wheel 62, stylet gear 64 and circular plate 66.

As shown in FIG. 2, stylet 42 is located in a circular stylet reel 46 which surrounds stylet connection 48. A portion of stylet 42 is trapped in a v-shaped groove 65 around the periphery of circular plate 66 such that rotation of stylet gear 64 and circular plate 66 extends stylet 42 through stylet channel 40 as described above. A proximal end 43 of stylet 42 is connected to stylet reel 46 to ensure that stylet 42 is pushed through stylet channel 40 as a result of rotation of circular plate 66. One suitable stylet 42 for use in the present invention may be a nitinol wire. Nitinol wire has certain characteristics which may be advantageous in the implementation of stylet 42 including rigidity in the axial direction but some flexibility in the radial direction. Essentially, stylet 42 must be sufficiently rigid when located in stylet channel 40 to stop movement of handle 24 when stylet 42 encounters an impediment in stylet channel 40. Rigidity of stylet 42 is enhanced by trapping the proximal end of stylet 42 in a channel 45 in stylet reel 46 and in v-shaped groove 65 in circular plate 66 such that stylet 42 cannot bend since the entire length of stylet 42 is then trapped either in the channel 45 in stylet reel 46, in v-shaped groove 65 in circular plate 66 or in stylet channel 40.

Rotation of gear wheel 62 due to movement of handle 24 also causes rotation of arm gear 68 via engagement of teeth 76 of gear wheel 62 with teeth 77 of arm gear 68. The gear plate of arm gear 68 includes a groove 80 into which arm 70 drops when handle 24 is moved to the start position shown in FIG. 3. Actuation shaft 86 is connected to an end of arm 70 via a rotatable connection 88 such that rotation of arm 70 translates to lateral movement of actuation shaft 86. Rotatable connection 88 permits the angle between actuation shaft 88 and arm 70 to change to accommodate rotation of arm 70. Actuation shaft 86 is involved in seed dispensing as will be described in greater detail below. When arm 70 drops into groove 80 in arm gear 68, this causes movement of actuation shaft 86 to the left in order to return actuation shaft 86 to a position which allows a seed cartridge to be docked with seed cartridge dock 20. A spring 84 is provided to help hold arm 80 in position against gear plate of arm gear 68.

Also shown in FIG. 3 is that lock release button 22 is attached to a shaft 90 provided with a spring 92 thereon. Shaft 90 is connected to a mechanical stop 94 such that depression of lock release button 22 moves mechanical stop 94 downwardly from the position shown in FIG. 3 to the position shown in FIG. 5. Gear wheel 62 includes a stop pin 96 thereon which engages mechanical stop 94 in the dispense position of handle 24 shown in FIG. 4 to prevent further rotation of handle 24 from the dispense position to the pack position until button 22 is depressed to move mechanical stop 94 out of the travel path of stop pin 96 as shown in FIG. 5.

FIG. 3 also shows that seed count indicator 26 is provided with a toothed wheel 120 thereon which rotates as seed count indicator 26 rotates. Toothed wheel 120 is adapted to engage ratchet 72 such that seed count indicator 26 is decremented by one each time handle 24 is moved from the dispense position of FIG. 5 to the start position of FIG. 4. Toothed wheel 120 also engages ratchet 74 each time handle 24 is moved from the transfer position shown in FIG. 6 to the start position shown in FIG. 3 to reset seed count indicator 26 to a count of two.

Figure 4:
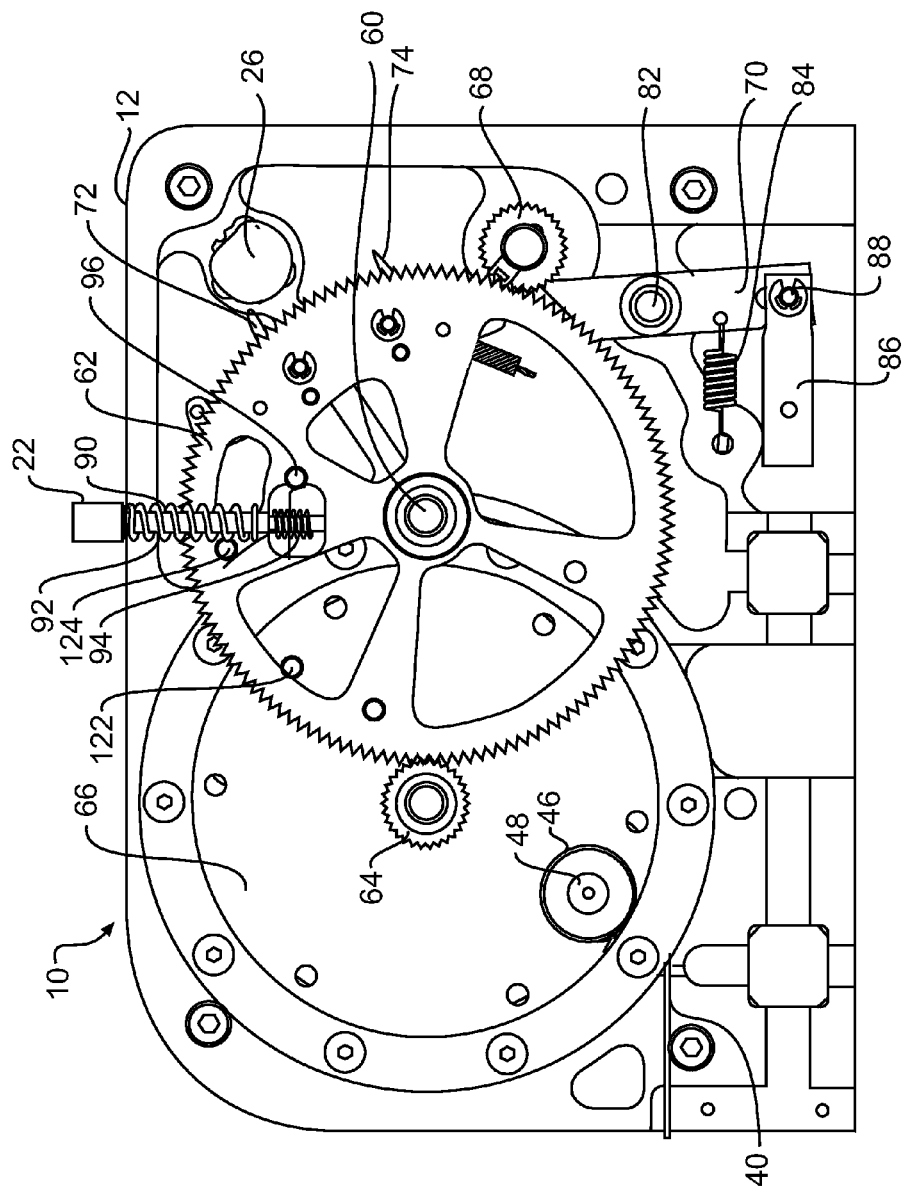
FIG. 4 is a view of the device of FIGS. 1A-2, from the reverse side with the housing removed showing the parts in the dispense position.
Figure 5:
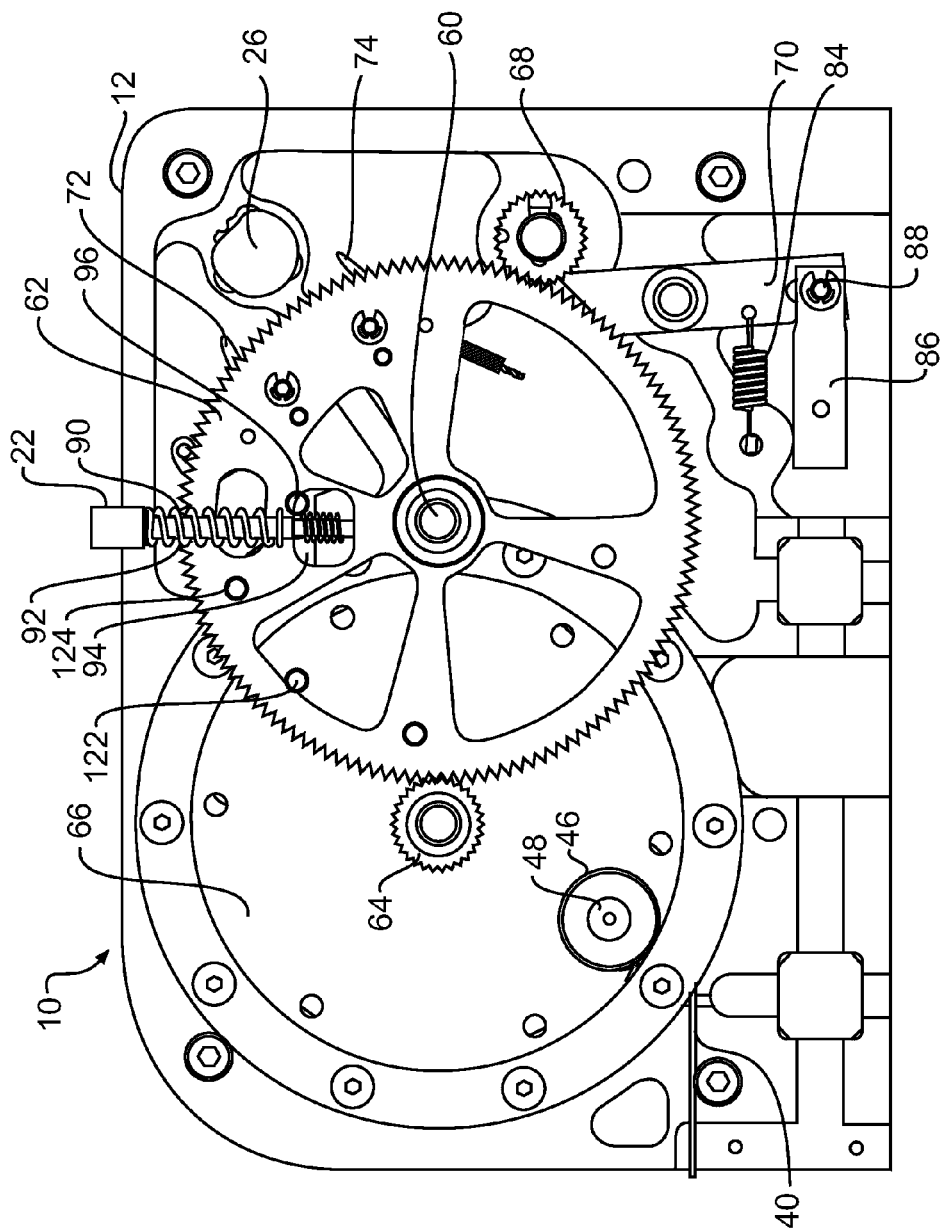
FIG. 5 is a view of the device of FIGS. 1A-2, from the reverse side with the housing removed showing the parts in the pack position.
Figure 6:
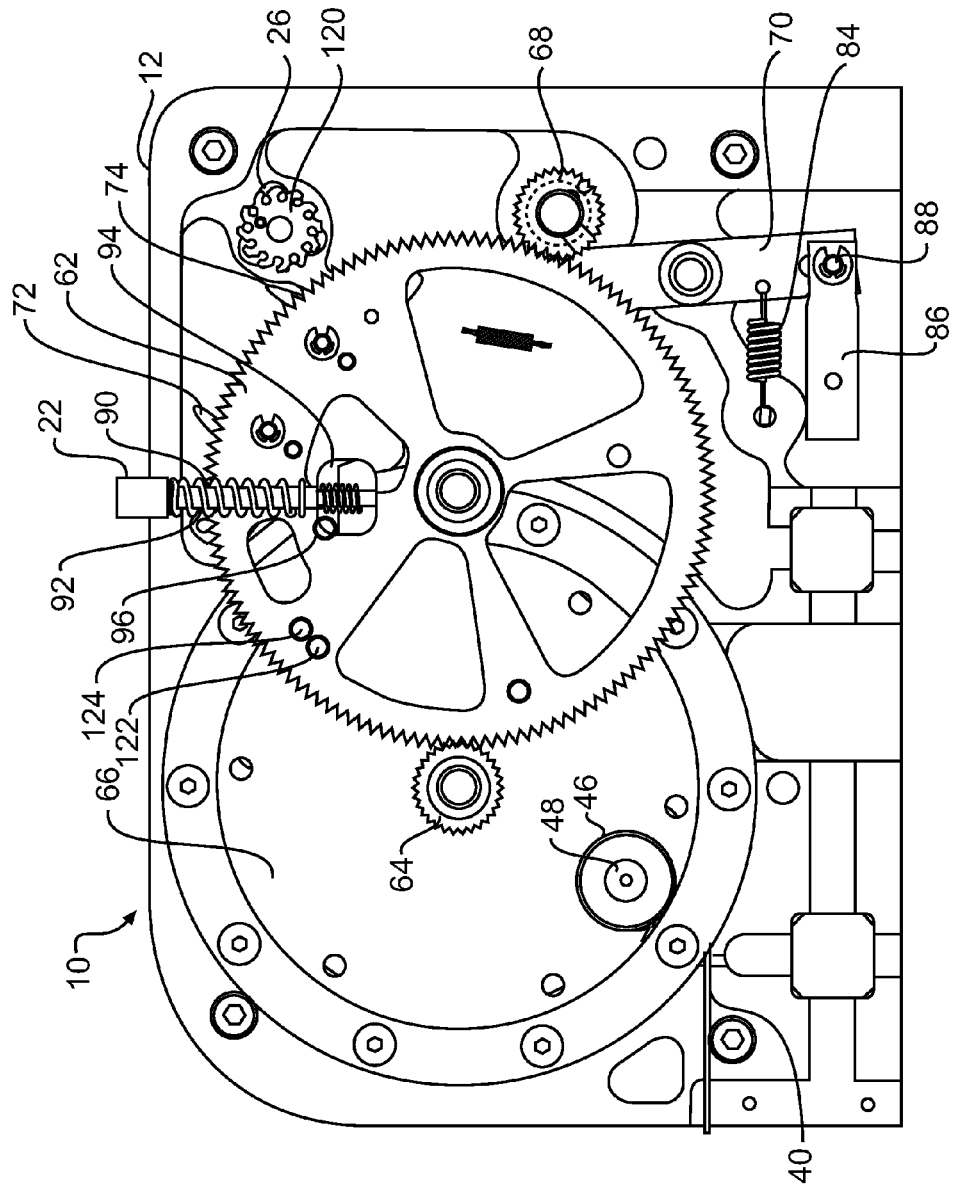
FIG. 6 is a view of the device of FIGS. 1A-2, from the reverse side with the housing removed showing the parts in the transfer position.

FIGS. 3-6 also show the end of stroke pin 122 and the back side of transfer stop pin 124 the function of which is described in relation to FIG. 6 below.

Referring to FIG. 4, device 10 is shown in the dispense position. As can be seen from FIG. 4, movement of handle 24 from the start position to the dispense position causes rotation of arm 70 about rotation point 82 and a corresponding lateral movement of actuation shaft 86. Initially, rotation of gear wheel 68 causes arm 70 to be pushed out of groove 80 in gear wheel 68 at which point arm 70 rides along the tangent edge of the gear plate of gear wheel 68. This causes actuation shaft 86 to move to the right from the position shown in FIG. 3 to the position shown in FIG. 4.

Also shown in FIG. 4 is that when handle 24 is moved to the dispense position, stop pin 96 engages mechanical stop 94 to prevent further movement of handle 24 to the pack position until button 22 is depressed to move mechanical stop 94 to a location below stop pin 96 as shown in FIG. 5.

Referring to FIG. 5, device 10 is shown with handle 24 in the pack position. As can be seen in FIG. 5, button 22 has been depressed to move mechanical stop 94 to a location below stop pin 96 to allow gear wheel 62 to travel in a counter-clockwise direction with handle 24 from the dispense position to the pack position. Also, it can be seen that arm 70 continues to ride along the tangent edge of gear wheel 68 as handle 24 is moved from the dispense position to the pack position thereby causing some further movement of actuation shaft 86 to the right.

Referring to FIG. 6, device 10 is shown in the transfer position. It can be seen that when handle 24 is located in the transfer position, transfer stop pin 124 reaches a position where it engages with end of stroke pin 122 to prevent further movement of gear wheel 62 in the counter-clockwise direction and thus prevent movement of handle 24 beyond the transfer position. Also shown in FIG. 6 is that ratchet 74 has passed toothed wheel 120 to thereby reset seed count indicator 26 from one to two.

Figure 14:
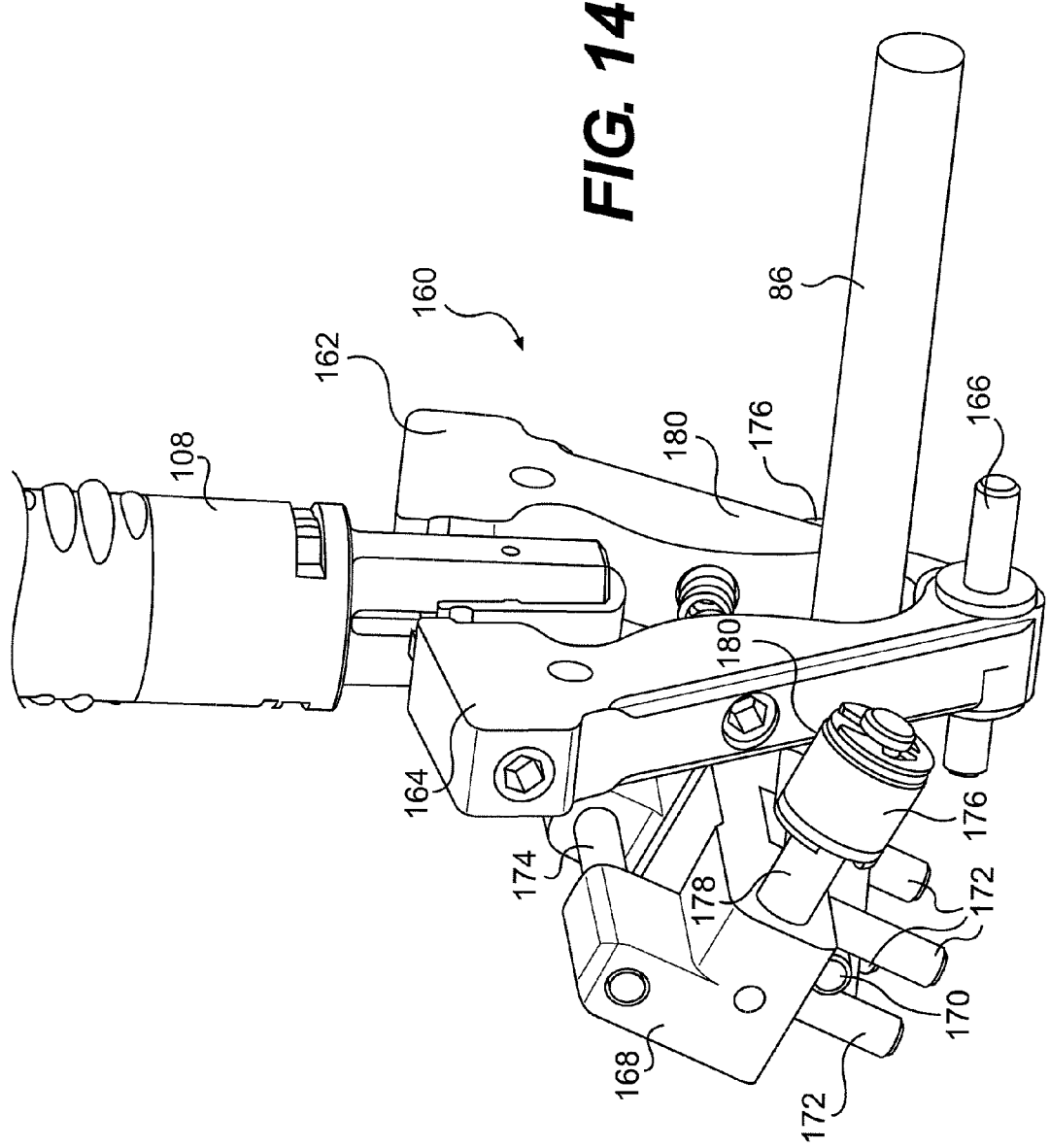
FIG. 14 is a side view of clip lock jaws for holding seeds for packing in the open position when the handle is in the start position.
Figure 15:
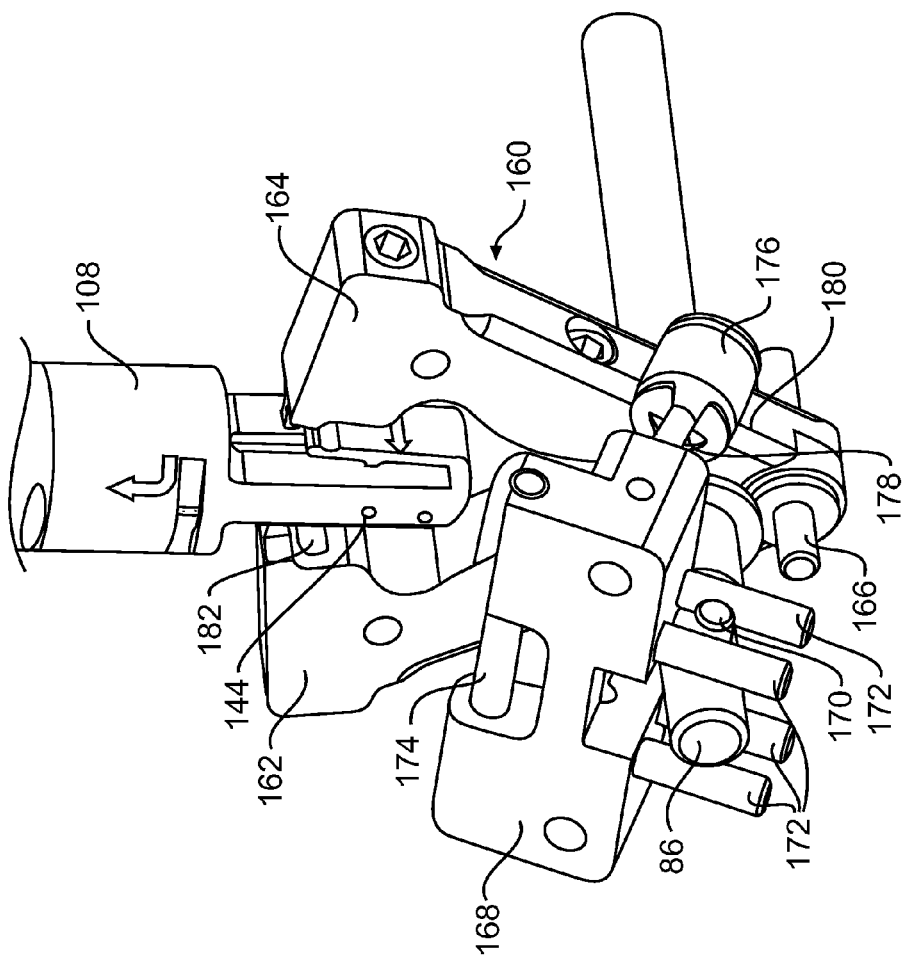
FIG. 15 is a rear perspective view of the clip lock jaws of FIG. 14 in the open position when the handle is in the start position.
Figure 16:
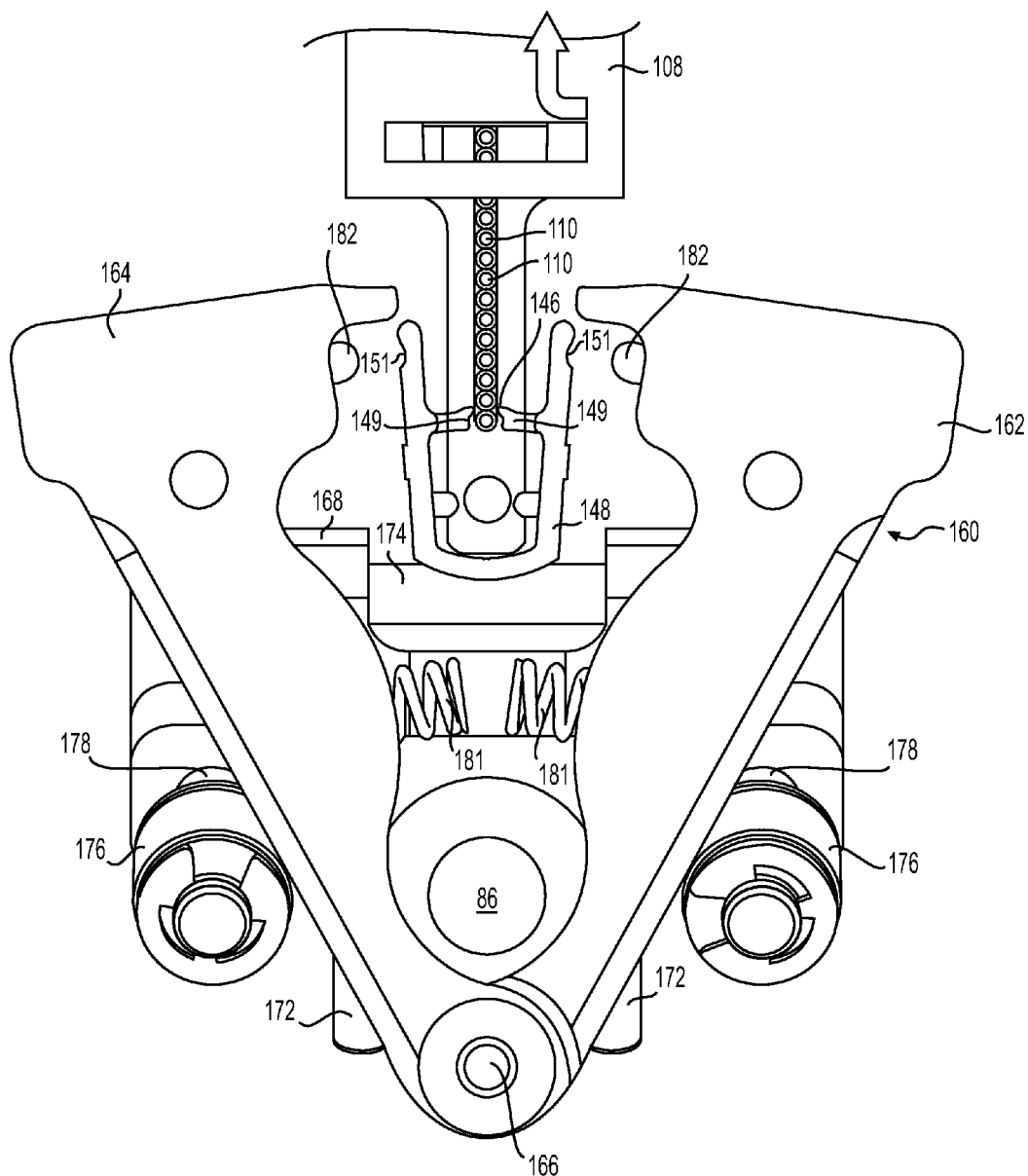
FIG. 16 is a front perspective view of the clip lock jaws of FIGS. 14-15 in the open position when the handle is in the start position.

The function of arm 70 and actuation shaft 86 are to actuate a mechanism that holds seeds 110 as they are dispensed from seed cartridge 108 for packing of a spacer 106 into end cap 223 of seed 110. One suitable mechanism for holding seeds 110 is shown in FIGS. 14-18. FIG. 14 shows a side view of clip lock mechanism 160 in the open position when handle 24 is located in the start position. Clip lock mechanism 160 is actuated by actuation shaft 86. Clip lock mechanism 160 includes locking jaws 162, 164 pivotally connected to one another by shaft 166 such that jaws 162, 164 open and close by pivoting about shaft 166. A toggle 168 is operably associated with actuation shaft 86 by link pin 170 that protrudes from both sides of actuation shaft 86 and rides in two sets of parallel tracks 172 attached to toggle 168, as best seen in FIG. 15. Toggle 168 is mounted for pivotal movement about toggle shaft 174 such that lateral movement of actuation shaft 86 to the right in FIG. 14 as a result of the connection of actuation shaft 86 to arm 70 described above, causes toggle 168 to pivot downwardly and to the right about toggle shaft 174. Toggle 168 includes a pair of rollers 176 attached to toggle 168 by shafts 178. Downward pivoting of toggle 168 causes rollers 176 to engage outer jaw surfaces 180 thereby squeezing jaws 162, 164 together from the open position shown in FIGS. 14-16 to the closed position shown in FIGS. 17-18. Jaws 162, 164 are biased to the open position by the action of springs 181.

Each of jaws 162, 164 is provided with press plungers 182 which are adapted to engage indentations 151 in flexible locking clip 148 when jaws 162, 164 are squeezed together by the action of rollers 176. When press plungers 182 engage indentations 151 in flexible locking clip 148, upper arms 145 of flexible locking clip 148 are pushed together from the open position shown in FIGS. 12 and 16 to the seed grasping position of FIG. 17 whereby fingers 149 grasp the seed 110 located in seed channel 142. The ends of fingers 149 are adapted to fit snugly with seed 110 to provide a firm grasp on seed 110 when locking jaws 162, 164 are in the closed position shown in FIG. 17. Locking jaws 162, 164 remain essentially in the closed position shown in FIG. 17 when handle 24 is in the dispensing, packing and transfer positions. However, when handle 24 is in the dispensing position, there is sufficient room between fingers 149 and/or sufficient flexibility in fingers 109 to allow a seed 110 to be pushed into seed channel 142 by seed plunger 150 for dispensing. In the dispensing position, fingers 149 exert a sufficient grasping force on seed 110 to permit packing of spacer 106 into end cap 223 of seed 110 before seed 110 comes free of the grasp of fingers 149. Once spacer 106 is packed into end cap 223 of seed 110, the force exerted on spacer 106 by stylet 42 with handle 24 in the dispense position is sufficient to push seed 110 out from between flexible fingers 149 and into strand assembly section 16. Seed plunger 150 can locate a new seed 110 between flexible fingers 149 with the jaws 162, 164 in the open position when handle 24 is in the start position. Jaws 162, 164 remain in the essentially closed position unless handle 24 is returned to the start position, at which point another seed can be positioned between flexible fingers 149 or a new seed cartridge 108 can be inserted into seed cartridge dock 20, if desired.

Figure 17:
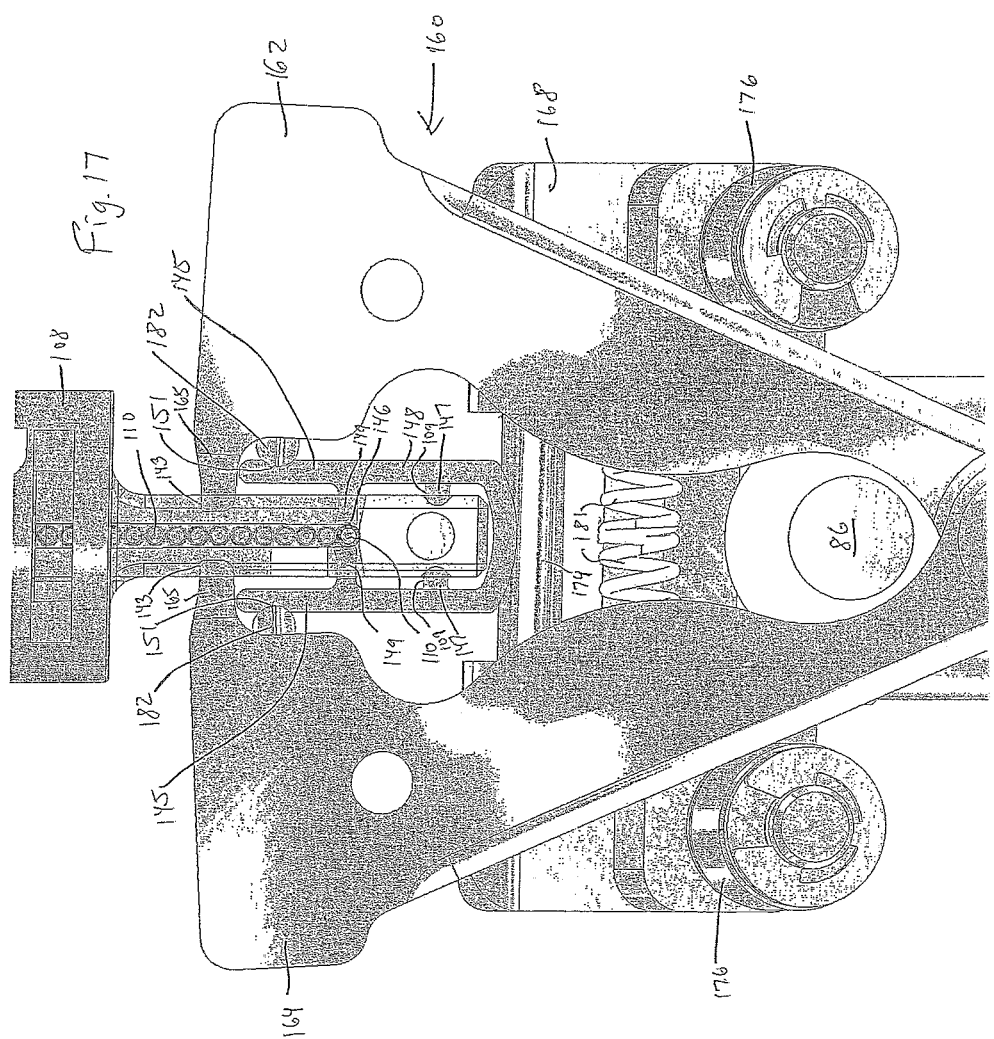
FIG. 17 is a front perspective view of the clip lock jaws of FIGS. 14-16 in the closed position held during dispense, pack and transfer positions of the handle.
Figure 18:
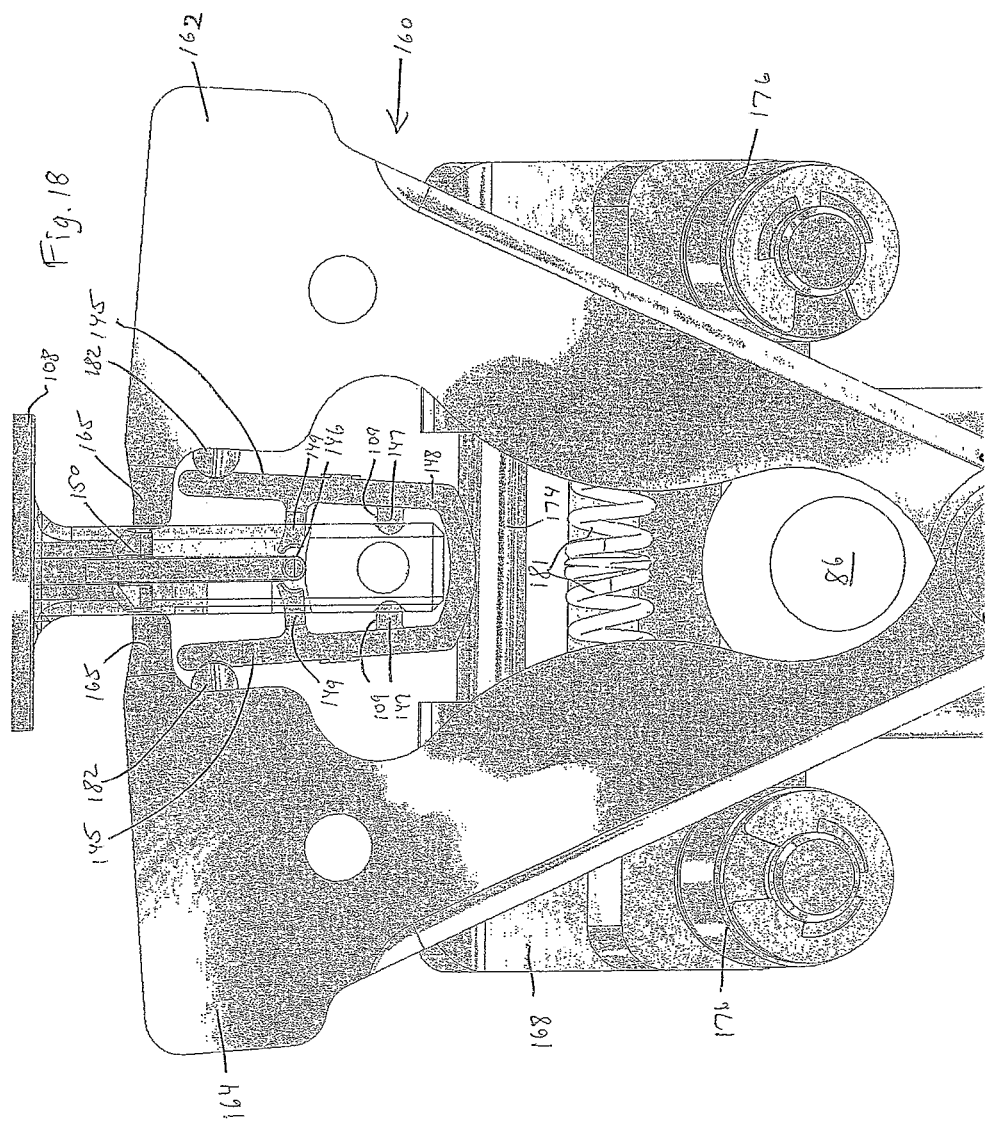
FIG. 18 is a front perspective view of the clip lock jaws of FIGS. 14-16 in the position when the seed magazine is empty.

Device 10 may include a force feedback mechanism that indicates that seed cartridge 108 is empty by force feedback from jaws 162, 164 all the way back to handle 24. Each locking jaw 162, 164 may include a feedback finger 165 located above press plungers 182. Feedback fingers 165 fit into corresponding slots 143 in seed cartridge 108 as shown in FIG. 17, when jaws 162, 164 are in the closed position. When seed cartridge 108 is empty, as shown in FIG. 18, seed plunger 150 is located at the height of feedback fingers 165 such that seed plunger 150 spreads feedback fingers 165 apart. This prevents locking jaws 162, 164 from reaching the fully closed position. As a result, rollers 176 and toggle 168 cannot rotate further forward thereby preventing actuation shaft 86 from moving in the horizontal direction in FIG. 14. This transfers force feedback via actuation shaft 86, arm 70, arm gear 68 and gear wheel 62 back to handle 24 such that the user feels sufficient resistance to the movement of handle 24 to indicate that seed cartridge 108 is empty. At this point, steps are taken to replace seed cartridge 108 and continue seed-stranding operations.

If it is desired to assemble strands with other, similar types of seeds and spacers, such as those described in U.S. Pat. Nos. 6,264,600 and 6,969,344, it is possible to reverse the locations of the seed cartridge dock 20 and spacer cartridge dock 18 and provide a mechanism for holding the spacers in position so that the seeds can be pushed into the cylindrical indentations in the ends of the spacers in much the same manner as described above, except with the seeds and spacers reversed.

Figure 19:
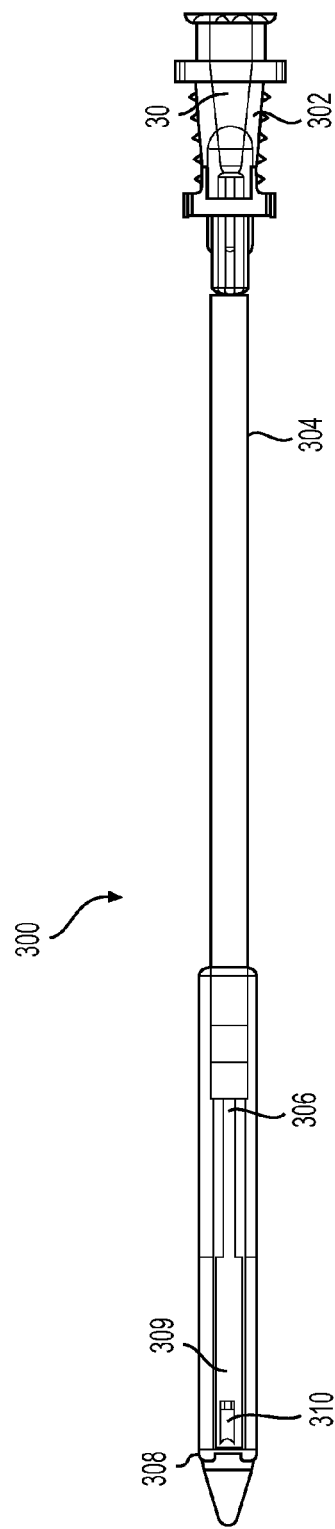
FIG. 19 is a top view of a transfer barrel in accordance with the present invention.
Figure 20:
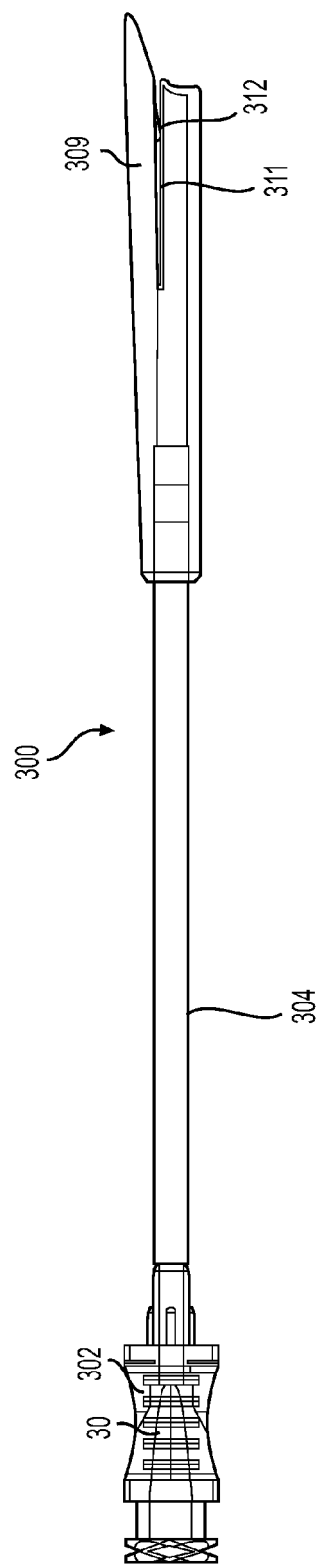
FIG. 20 is a side view of the transfer barrel of FIG. 19.
Figure 21:
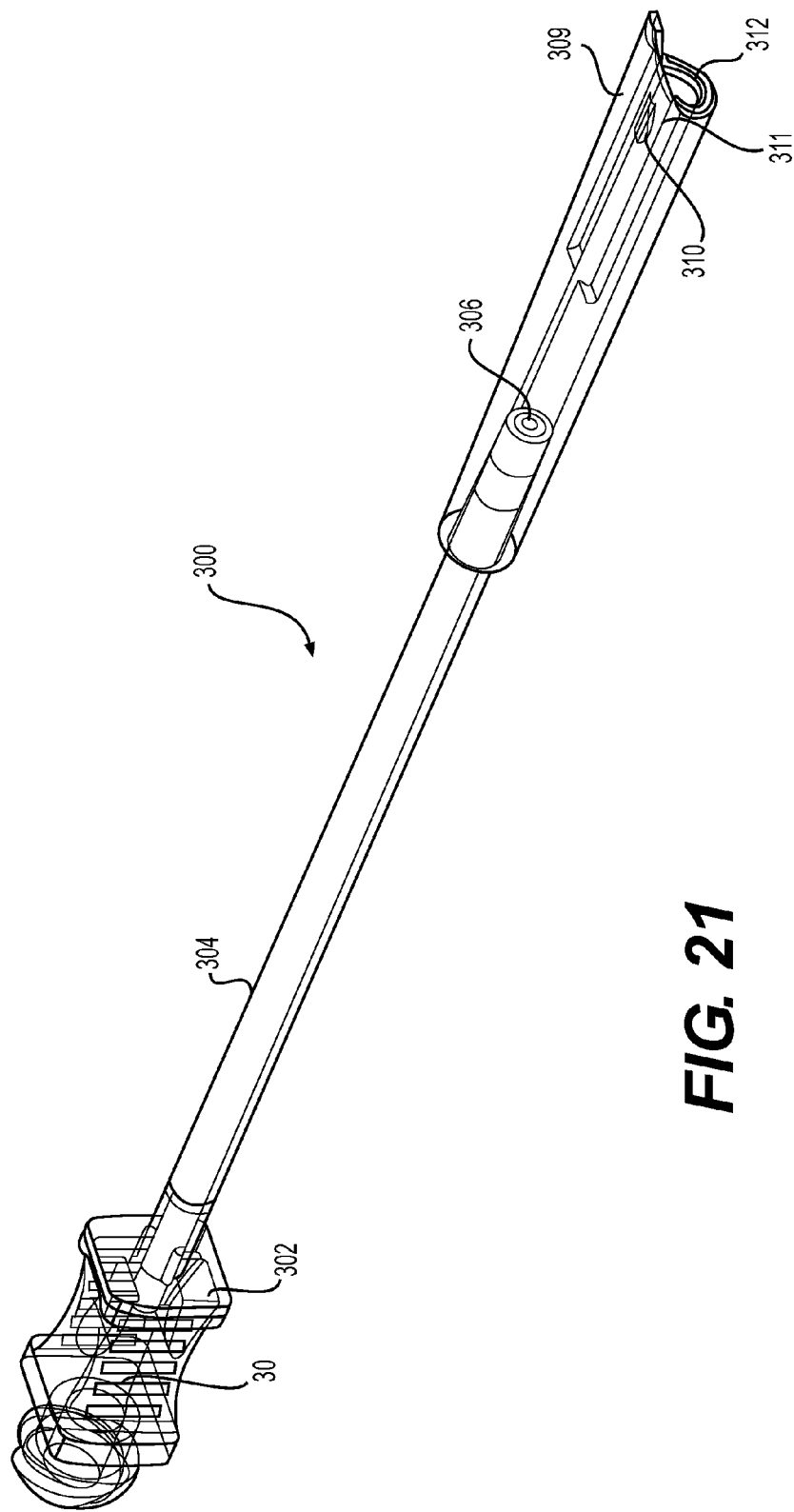
FIG. 21 is a perspective view of the transfer barrel of FIGS. 19-20.
Figure 22:
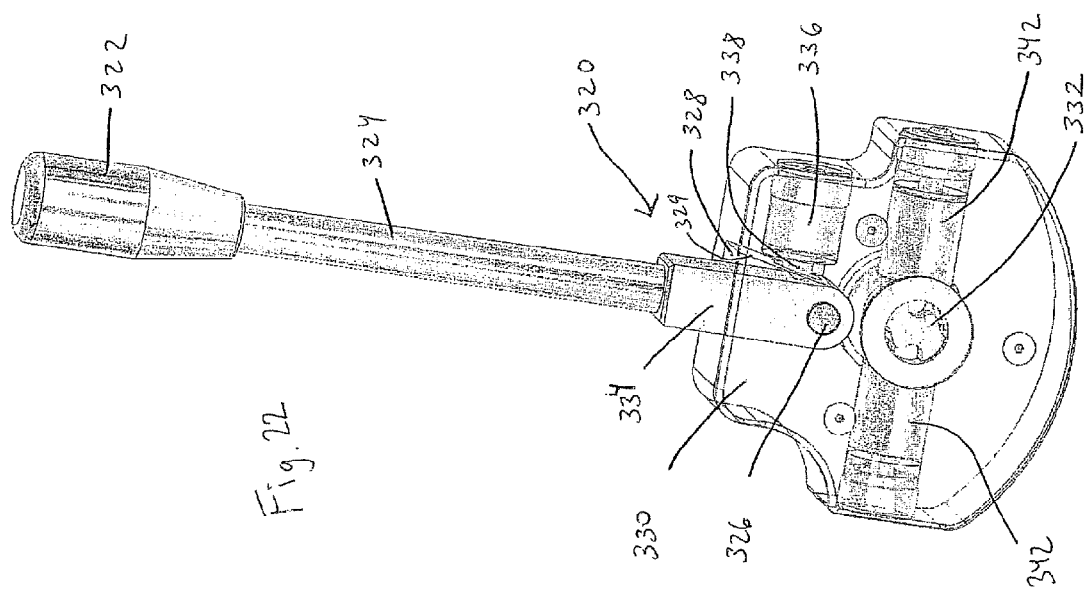
FIG. 22 is a perspective view of an alternative torque handle assembly with a transparent housing to show internal parts thereof.
Figure 23:
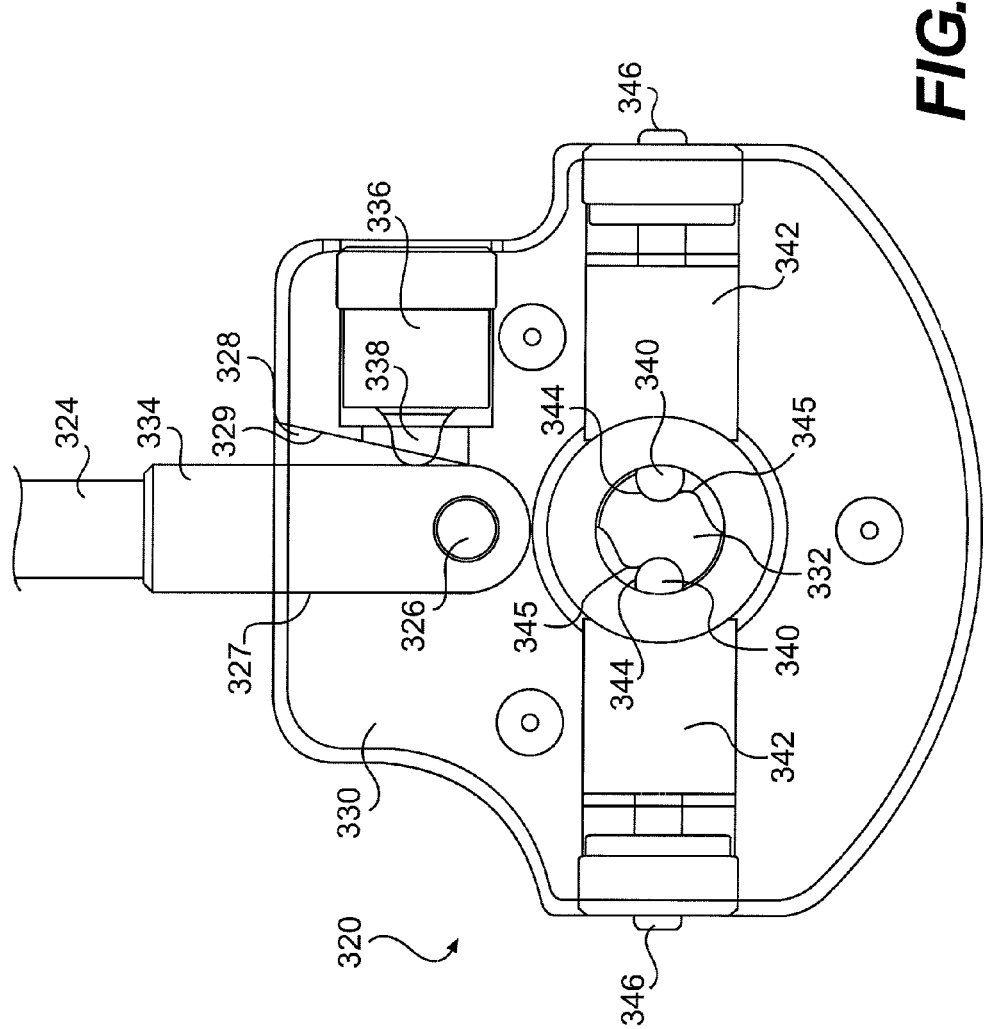
FIG. 23 is a front view of the torque handle assembly of FIG. 22 in the start position with a transparent housing to show internal parts thereof.

Strand outlet 30, as shown in the figures, is provided with a suitable connection mechanism, such as a luer lock, for connecting a transfer barrel 300 or needle to strand outlet 30. An example of a suitable transfer barrel 300 is shown in FIGS. 19-21. Transfer barrel 300 includes, for example, a luer lock connection 302 or other suitable connection at the proximal end thereof for connection to strand outlet 30 of device 10. Conventional luer lock connections known to persons skilled in the art may be employed for this purpose. Transfer barrel 300 also includes an outer rigid tube 304, which may be made of steel, having a sterilizable plastic tube 306 located therein.

A distal end 308 of plastic tube 306 is preferably at least slightly flexible to permit transfer barrel 300 to be easily connected to a conventional brachytherapy needle or, for example, a Mick applicator since transfer barrel 300 may be used as a temporary holding device to transfer an assembled strand to a brachytherapy needle which has preferably already been placed in the patient. Then, a stylet (not shown) is used to push the strand from the transfer barrel into the brachytherapy needle and the brachytherapy needle is then retracted, holding the stylet in place, to deploy the strand in the patient.

A Mick applicator may slide over a piece of plastic on the end of the needle. A tooth or dog drops down behind the plastic hub of the needle to capture the needle in the Mick applicator. Users often prefer to pre-position needles in the patient before putting seeds or seed strands into the needles. This allows the user to take their time positioning the needle and to view the needle to ensure that it is in the proper location in accordance with the treatment plan. Also, with an empty needle, the piercing of a blood vessel can be detected since blood will flow through the empty needle to the proximal end and be seen by the user.

Transfer barrel 300 may be used to facilitate loading of assembled strands into pre-placed needles of various designs, including Mick needles provided with a cylindrical hub designed for placement using the Mick applicator device. Strands permit more accurate placement of seeds using needles since the rigidity of the strand and the use of spacers both lead to more accurate positioning of seeds. Distal end 308 of transfer barrel 300 is adapted for mounting onto a needle which may be pre-positioned in the patient or otherwise. A variety of different mounts on the ends of needles can be accommodated by transfer barrel 300 of the present invention, including for example, glued, press-fit, a luer lock, etc.

Distal end 308 of transfer barrel 300 includes a flexible portion 309 which is deformable since it is made of a suitable deformable material and because of the provision of slots 311 in transfer barrel 300. The proximal end of a needle provided with a hub can be inserted into distal end 308 of transfer barrel 300. Insertion of the hub will force flexible portion 309 upward to allow passage of the hub into transfer barrel 300 a sufficient distance such that a distal end of the hub passes dog 310 on flexible portion 309 at which point dog 310 drops down behind the distal end of the hub to retain the hub in the transfer barrel 300 by engagement of dog 310 with a surface of the hub.

Internal plastic tube 306 may be fabricated with a tightly controlled inner diameter of, for example, about 0.032-0.034 inches (0.0812 to 0.0864 cm) for the purpose of holding the strand in plastic tube 306 and to prevent the strand from falling out of plastic tube 306. Specific materials and/or structure may be selected for plastic tube 306 to create static forces with the strand and/or to provide a slight bend in plastic tube 306 to hold the strand in place. Also, the strand itself may bend a bit to further facilitate its own retention in plastic tube 306. Careful fabrication of plastic tube 306 in this manner eliminates the need for bone wax, clips, valves, gates, switches or another sealing mechanism to retain the assembled strand in internal tube 306 of transfer barrel 300 during transfer from device 10 to a needle or other destination. Internal tube 306 is preferably fabricated from a medical grade material which may be selected from, for example, polycarbonate, polystyrene, acrylic, polyimide, polyamide, polysulfone, polyethersulfone and polyolefin. The plastic materials have the advantages that they are less rigid than steel and because they are extrudable, are much simpler to manufacture than steel tubes. Alternatively, internal tube 306 could be manufactured from any other suitable material such as steel, aluminum, brass, silicon, etc.

In another embodiment, transfer barrel is made with a single steel tube with no inner tube and the steel tube is provided with the correct diameter, e.g. 0.032-0034 inches (0.0812 to 0.0864 cm), to accomplish retention of the assembled strand in transfer barrel 300 during transfer.

FIGS. 22-25 show torque handle assembly 320 which can be used as an alternative to replace handle 24 described above. Torque handle assembly 320 includes a grip 322, and an arm 324 pivotally mounted on arm pivot 326 via a base portion 334 for movement within arm slot 328 provided in handle housing 330. Handle housing 330 is coupled to gear wheel 62 of device 10 via a profile shaft 332. Torque handle assembly 320 may be provided with a tactile feedback mechanism to give the user an indication of when sufficient force has been exerted on grip 322 and arm 324 to accomplish packing of the seed strand.

For example, tactile feedback mechanism may include a casing 336 which houses a spring (not shown) connected to a tactile plunger 338. As the user exerts force on the grip 322 and arm 324, base portion 334 rotates to the right in arm slot 328, as shown in the figures, and abuts with tactile plunger 338 to exert a force thereon. The spring inside casing 336 applies resistance to tactile plunger 338 at a preset force lower than the force required to cause profile plungers 340 to slip. The tactile plunger 338 compresses causing the base portion 334 to rotate with slightly less force than is needed to slip the clutch by causing profile plungers 340 to slip. This lets the operator know that the full force required for packing the seed strand has been reached by providing increased resistance to the grip 322 and arm 324 of the torque handle assembly 320.

Torque handle assembly 320 may be provided with a slip mechanism to prevent exertion of too much force on the seed strand during packing and/or transfer of the seed strand to prevent breaking of seeds or spacers during these steps. Slip mechanism involves profile shaft 332, profile plungers 340 and a pair of springs located in profile casings 342. In the start position shown in FIG. 21, profile plungers 340 are located in corresponding indentations in the profiles 344 of profile shaft 332. Each profile plunger 340 is spring loaded against a spring located inside profile casings 342. The spring force of the springs located in profile casings 342 is greater than the spring force set for the spring which loads the tactile plunger 338. As the torque handle assembly 320 is rotated, profile plungers 340 are pressed against the springs until profile plungers 340 are moved a sufficient distance that they can ride along the profiles 344 of profile shaft 332 to a peak maximum force. When profile plungers 340 pass the peaks 345 of profile shaft 332, the torque handle assembly 320 is designed to decouple from the drive gear as a result of the profiles 344 of profile shaft 332.

Referring to FIG. 21, the torque handle assembly 320 is shown in the start position. In this position, base portion 324 is against the leftmost wall 327 of slot 328, as shown, and profile plungers 340 are located in corresponding indentations in profiles 344 of profile shaft 332. As the user moves the torque handle assembly 320 to the pack position shown in FIG. 24, base portion 324 exerts force against tactile plunger 338 as it pivots to the right about arm pivot 326. This provides force feedback to the user via torque handle assembly 320 as described above. Once the pack position is reached, base portion 324 abuts against the rightmost wall 329 of slot 328 to prevent further movement of base portion 324 to the right. In addition, movement of arm 324 exerts force on profile plungers 340 which will ride along profiles 344 of profile shaft 332 as shown in FIG. 24 as the force on profile plungers 340 depresses these plungers 340 against the spring force exerted thereon.

Referring to FIG. 25, torque handle assembly 320 is shown in the clutch slip position where the profile plungers 340 reach a peak 345 on profiles 344 at which a maximum force is exerted on profile plungers 340. If profile plungers 340 move further along profile 344, profile 344 allows a clutch slip whereby the force is released or reduced to prevent damage to the strand components by exertion of too much force thereon. As shown in FIGS. 24-25, each of the springs may include set screws 346 for separately adjusting the amount of force required to engage either the tactile feedback mechanism or the clutch slip mechanism. A torque mechanism of this type can be used for many applications other than in the present device where torque limitation is required.

It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A system for preparation of strands of radioisotope seeds and spacers, comprising:
    a seed cartridge receiving structure;
    a spacer cartridge receiving structure;
    a user-actuated apparatus for dispensing seeds and spacers from cartridges located in said seed and spacer cartridge receiving structures and preparation of a strand from said dispensed seeds and spacers in a strand assembly section;
    an alignment mechanism for aligning said seeds and spacers to permit assembly of strands from seeds and spacers having end portions adapted to mechanically interact to hold said seeds and spacers together in said strand, wherein said alignment mechanism comprises a seed channel inlet having a diameter less than the outside diameter of the larger of a spacer or a seed outside diameter; and further comprising a mechanism to prevent said strand from being dispensed from a seed stranding section including a seed counter to prevent dispensing of more than a predetermined number of seeds, wherein the seed counter counts each dispensed seed.

2. The system as claimed in claim 1, wherein said seed counter can be indexed to increase or decrease the number of seeds in a particular strand once strand assembly has commenced.

3. The system as claimed in claim 1, wherein said mechanism to prevent said strand from being dispensed from said seed stranding section comprises a mechanical stop operatively associated with said seed counter such that said mechanical stop cannot be moved until said seed counter indicates a predetermined value.

4. The system as claimed in claim 1, wherein said mechanism to prevent said strand from being dispensed from said seed stranding section further comprises an actuator for actuation of a mechanical stop to allow said strand to be dispensed from said seed stranding section.

5. The system as claimed in claim 1, wherein said mechanism prevents further dispensing of seeds by said user-actuated apparatus when said seed counter indicates a predetermined value until said strand has been dispensed from said seed stranding section.

6. The system as claimed in claim 1, wherein said seed channel inlet aligns said spacers and seeds concentrically about a longitudinal axis of said spacers and seeds.

7. The system as claimed in claim 6, wherein said alignment mechanism further comprises a seed or spacer holder which holds the seed or spacer which has the largest outside diameter in alignment with said seed channel inlet.

8. The system as claimed in claim 7, wherein said seed or spacer holder holds said seed or spacer with sufficient force to allow the other of said seed or spacer to be mechanically engaged with said held seed or spacer by pushing of the other of said seed or spacer against said held seed or spacer.

9. The system as claimed in claim 1, further comprising:
a force-limiting mechanism operatively associated with a user-actuated mechanical apparatus for dispensing seeds and preparation of a strand from said dispensed seeds, said force-limiting mechanism preventing exertion of greater than a predetermined amount of force on said seeds and spacers during strand preparation.

10. The system as claimed in claim 9, wherein said user-actuated mechanical apparatus for dispensing seeds and spacers and preparation of a strand from said dispensed seeds and spacers comprises a handle operatively connected to a stylet to allow said handle to advance said stylet to dispensing and strand preparation positions.

11. The system as claimed in claim 10, wherein said force-limiting mechanism disengages the operative connection between said handle and said stylet when a predetermined amount of force is exerted on said stylet by said handle.

12. The system as claimed in claim 11, wherein said force-limiting mechanism includes one of a clutch and a leaf spring for disengaging the operative connection between said stylet and said handle.

13. The system as claimed in claim 11, wherein said force-limiting mechanism comprises an adjustment mechanism to allow adjustment of the predetermined force which may be exerted on said stylet by said handle during strand preparation.

14. The system as claimed in claim 1, further comprising:
a restraint to prevent a user-actuated mechanical apparatus from moving from a dispense position to a pack position until a user-actuated restraint is actuated by a user.

15. The system as claimed in claim 14, wherein said seed and spacer cartridges can be removed from said seed and spacer cartridge receiving structures when said user-actuated mechanical apparatus for dispensing seeds and spacers and preparation of strands is in the dispense position to allow use of a variety of different seeds and spacers in a strand assembly.

16. The system as claimed in claim 15, wherein said restraint comprises a mechanical stop mechanism connected to a button which can be actuated by a user.

17. The system as claimed in claim 1, further comprising:
a seed cartridge;
a spacer cartridge;
wherein said user-actuated apparatus is configured for dispensing seeds and spacers from said seed and spacer cartridges located in said seed and spacer cartridge receiving structures and preparation of a strand from said dispensed seeds and spacers in a strand assembly section;
wherein at least one of said seed and spacer cartridges includes a device for indicating when said seed or spacer cartridge is empty; and
a feedback mechanism operatively associated with said device for indicating when said seed or spacer cartridge is empty for providing mechanical feedback to a user of said system indicating that one of said seed and spacer cartridges is empty.

18. The system as claimed in claim 17, wherein at least one of said seed and spacer cartridges comprises a dispensing channel and said device of said seed or spacer cartridge for indicating when said seed or spacer cartridge is empty comprises a structure that blocks said dispensing channel.

19. The system as claimed in claim 18, wherein the structure that blocks the dispensing channel is a plunger which also functions to urge at least one seed or spacer toward the dispensing channel when at least one seed or spacer is present in said cartridge.

20. The system as claimed in claim 17, wherein at least one of said seed and spacer cartridges comprises a holder for holding a seed or spacer in a dispensing position, said holder comprising a structure for engaging a plunger when said cartridge is empty, said feedback mechanism is operatively associated with said holder to provide feedback when said structure engages said plunger, and said plunger also functions to urge at least one seed or spacer toward a dispensing channel in said cartridge when at least one seed or spacer is present in said cartridge.

21. The system as claimed in claim 1, wherein the seeds that are adapted to mechanically interact have end cups and the spacers that are adapted to mechanically interact have ribs.

* * * * *